United States Patent [19]

Shimazu et al.

[11] Patent Number: 5,680,867
[45] Date of Patent: Oct. 28, 1997

[54] ELECTRONIC BLOOD PRESSURE MEASURMENT DEVICE

[76] Inventors: Hideaki Shimazu, 14-11, Gotokuji 1-chome Setagaya-ku, Tokyo 154; Hidetaka Shimizu, 744-1, Yokosawa-cho Nagano-shi, Nagano 380; Noriyuki Yamaguchi, 2844-3, Noborito, Tama-ku Kawasaki-shi, Kanagawa 214; Masaru Komatsu, 4880-7, Osachi, Okaya-shi, Nagano 394, all of Japan

[21] Appl. No.: 347,428

[22] PCT Filed: Apr. 1, 1994

[86] PCT No.: PCT/JP94/00545

§ 371 Date: Feb. 13, 1995

§ 102(e) Date: Feb. 13, 1995

[87] PCT Pub. No.: WO94/22363

PCT Pub. Date: Oct. 13, 1994

[30] Foreign Application Priority Data

Apr. 2, 1993 [JP] Japan ............... 5-100444

[51] Int. Cl.⁶ ............................................ A61B 5/00
[52] U.S. Cl. ............... 128/672; 126/677; 126/650; 126/681; 126/691; 126/687; 126/713
[58] Field of Search .................... 128/672, 677, 128/680–3, 687–690, 713

[56] References Cited

U.S. PATENT DOCUMENTS

| | | | |
|---|---|---|---|
| 4,349,034 | 9/1982 | Ramsey, III | 128/681 |
| 4,922,918 | 5/1990 | Ruiter | 128/681 |
| 5,092,343 | 3/1992 | Spitzer et al. | 128/702 |
| 5,339,818 | 8/1994 | Baker et al. | 128/680 |
| 5,390,679 | 2/1995 | Martin | 128/713 |
| 5,406,952 | 4/1995 | Barnes | 128/672 |
| 5,533,511 | 7/1996 | Kasperi et al. | 128/687 |

FOREIGN PATENT DOCUMENTS 0197302  3/1986  European Pat. Off. .

*Primary Examiner*—Robert Nasser
*Attorney, Agent, or Firm*—Dorn, McEachran, Jambor & Keating

[57] ABSTRACT

In an electronic blood pressure measurement device which is arranged to extract pulse waves from the measured cuff pressure, a pulse wave pattern is generated from the pulse wave amplitude and pulse wave interval data and this pulse wave pattern is compared with reference patterns to classify the pattern in order to accurately obtain biological information other than the blood pressure. Blood pressure amplitudes PA(i) are computed from the measured cuff pressures C(i) and a pulse wave pattern is generated (35) on the basis of this pulse wave amplitude data and this pulse wave pattern is classified into a plurality of reference patterns (37) according to reference patterns or reference values (36). Here, the reference patterns or reference values are set as hemodynamic references based on dynamic characteristics of the blood vessel or cardiac output characteristics. The pulse wave pattern is normalized as necessary to extract only the shape factors of the pattern, is displayed as a measured pattern corresponding to a reference pattern and is compared with the reference patterns in terms of shape. Also, besides the shape factors, the absolute values of pulse wave amplitudes and systolic pressures are used as references for pattern classification.

5 Claims, 16 Drawing Sheets

| Type | Reference pulse wave pattern | Pulse wave pattern | Presumed disease |
|---|---|---|---|
| A | | | Normal |
| B | | | Anemia, hypotension, shock |
| C | | | Arteriosclerosis, obesity, senescence, heavy stress |
| D | | | Arrhytmia |
| E | | | Cardiopathy |

FIG. 9

| Type | Reference pulse wave pattern | Pulse wave pattern | Presumed disease |
|---|---|---|---|
| A | | | Normal |
| B | | | Anemia, hypotension, shock |
| C | | | Arteriosclerosis, obesity, senescence, heavy stress |
| D | | | Arrhytmia |
| E | | | Cardiopathy |

FIG. 11
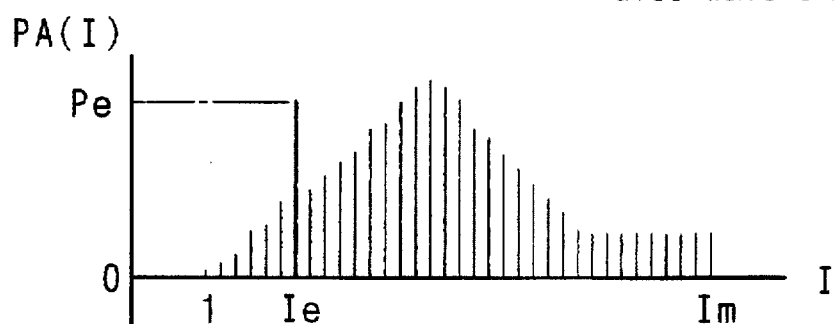
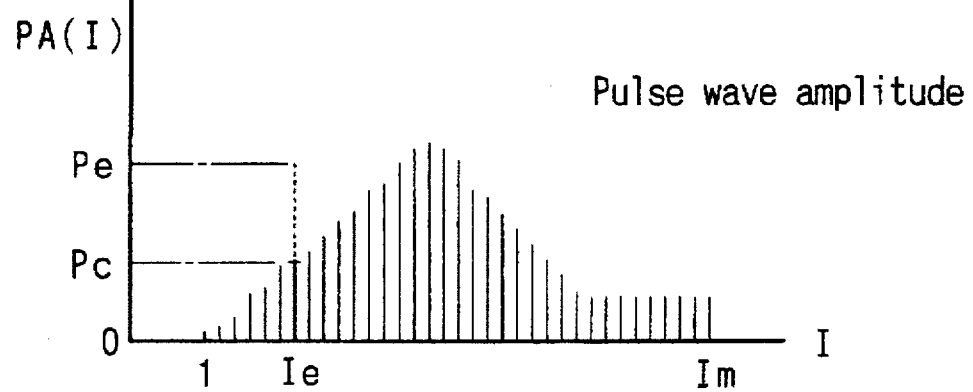
FIG. 12
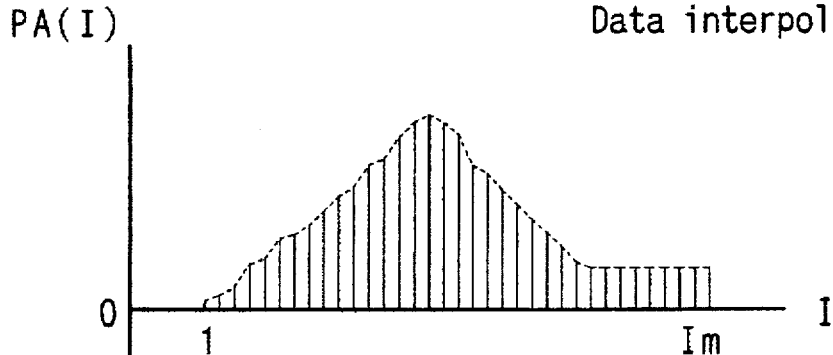
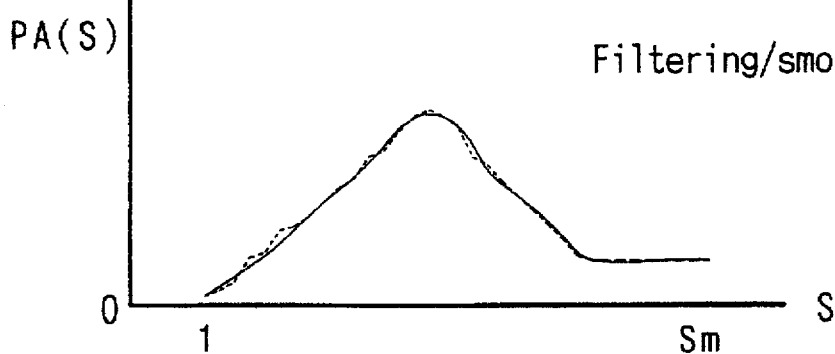

5,680,867

ELECTRONIC BLOOD PRESSURE MEASURMENT DEVICE

TECHNICAL FIELD

The present invention relates to an electronic blood pressure measurement device which detects the cuff pressure for the evaluation of vascular dynamics and is concerned in particular with an improved device for obtaining biological information besides blood pressure, etc. on the basis of pulse wave components extracted from the cuff pressure.

PRIOR ARTS

Conventional devices for non-invasive measurement of vascular dynamics include that which detects the Korotkoff's sound that is generated by the pulse waves within the blood vessels during the process of gradually decreasing the pressure of a pressurized cuff. In such a device, the pressures at the points in time at which the Korotkoff's sound is generated, becomes the maximum and disappears are detected to obtain the systolic blood pressure, the mean blood pressure and the diastolic blood pressure. However, detection errors occur easily in this method since the Korotkoff's sound is a minute sound in a frequency band that is easily influenced by external noise and this method has such problems as large detection errors and poor reproducibility since the decay of sound waves differ greatly according to the detected part and the thickness of the superficial tissue.

Thus, in recent years, the oscillometric method has come to be used in which the blood pressure, etc. are directly computed from the variations in the cuff pressure. In this method, the pulse waves that are overlaid onto the detected cuff pressure are extracted to derive the amplitudes of the pulse waves and the pressures at the points at which the pulse wave amplitude is the maximum, at which the amplitude is a predetermined proportion of the maximum value at the higher pressure side of the maximum and at which the amplitude is a predetermined proportion of the maximum pressure at the lower pressure side of the maximum are determined as the mean blood pressure, systolic blood pressure and diastolic blood pressure, respectively. Sphygmomanometers that use this method are not easily affected by external influences such as external noise and vibration and enable measurements of high accuracy and reproducibility since highly sensitive pressure sensors can be used and since the detected signals are in a low frequency band.

Most of the measurement devices of the said type perform only the detection of the systolic pressure, the diastolic pressure, the mean blood pressure and the pulse rate. However, since these values are influenced by various factors such as cardiac output and degree of hardening of the arteries and the influence of such factors cannot be judged by simply measuring the blood pressure, it is not only impossible to correctly evaluate the blood pressure value but it is also impossible to obtain a correct understanding of the vascular dynamics.

Also, particularly in the case of measurement devices using the oscillometric method, the blood pressure values are computed generally by a predetermined method that is based on comparison with a direct method such as that in which a catheter is inserted. However, such a method has a problem in that, due to variations in the pattern of pulse wave amplitudes, cases arise that do not correspond with values detected by the direct method.

Furthermore, the mechanism of generation of Korotkoff's sounds and pulse wave amplitudes has not been investigated in detail and the present circumstances are such that the relationships between measured data and the cause thereof are judged experientially and case by case.

The present invention is one that solves the said problems and the purpose thereof is to provide a measurement device that can extract information reflecting the vascular dynamics from pulse wave amplitude patterns on the basis of the knowledge obtained through the clarification of the mechanism of generation of pulse amplitudes to provide indications for such measured values as the blood pressure.

DISCLOSURE OF THE INVENTION

The present invention provides a pressure detection means (12, 16, 17:23) that detects the cuff pressure under the influence of the pulse wave during the process of gradually decreasing or increasing the cuff pressure, a pulse wave extraction means (24) that extracts the pulse wave components from the cuff pressure detected by said pressure detection means, a pulse wave amplitude detection means (27) that detects the pulse wave amplitudes which express the values corresponding to the amplitude of each pulse of the pulse wave component extracted by said pulse wave extraction means and a pattern classification means (37) that classifies the pulse wave patterns, that express the pulse wave amplitude variations on the basis of the pulse wave amplitudes, according to reference patterns that are set as hemodynamic references based on dynamic characteristics of blood vessels and/or cardiac output characteristics. Thus, by the present invention, not only are pulse wave patterns used simply to judge the blood pressure values as was done conventionally, but it also becomes possible to extract information reflecting the vascular dynamics by the classification of pulse wave patterns according to the shapes of the patterns. It also becomes possible to know the meaning and the reliability of the blood pressure value judged by the shape of the pulse wave pattern.

A pulse wave pattern generation means (32, 33, 35, 36, 1005, 1006), that generates pulse wave patterns that are normalized by predetermined reference values on the basis of pulse wave amplitudes and pulse wave intervals, is also provided in the present invention. In this case, it is preferable to provide in the pulse wave pattern generation means, a pulse wave pattern normalization means (1005, 1006) that normalizes the pulse wave amplitudes and the pulse wave intervals. Although widely varying pulse wave patterns are obtained due to measurement conditions and individual differences (pulse rates, blood outputs, blood pressure amplitudes), the provision of a pulse wave pattern normalization means enables accurate classification of patterns by enabling comparisons of only the shapes of the patterns.

Furthermore, it is preferable to normalize the reference pattern in the same manner as the normalized pulse wave pattern and for the pulse wave pattern classification means to use the correlation between a plurality of reference patterns and the normalized said pulse wave pattern as a classification reference. Accurate pattern classification based only on the shape of the pattern is enabled by classifying on the basis of the correlation with the reference patterns that are normalized in the same manner. In particular, by using the position of the maximum value of the pulse wave amplitudes as a basis to normalize each of the said pulse wave intervals prior and subsequent to said position, errors in the comparison of patterns due to deviations in the peak positions can be avoided.

It is preferable to set a plurality of reference patterns according to the shape of the peak of the pulse wave amplitude. The peak shape of the pulse wave amplitude reflects information, particularly on the expandability of the blood vessel.

It is also effective to provide a quantization means (29, 30, 31) that quantizes the pulse wave amplitudes and/or pulse wave intervals and transmits the quantized data to the pulse wave pattern generation means. By providing a means for quantizing the detected data, the high data resolution, which is not necessarily required for the subsequent processes of pulse wave pattern generation and classification, can be reduced to some degree to enable reductions in the processing time and the memory capacity.

In the above cases, it is preferable to provide in the pattern classification means, a means (1022) for detecting the number of peaks and/or the degree of disturbance of pulse wave patterns and to perform the classification (1023, 1024) of pulse wave patterns using the number of peaks and/or degree of disturbance as part of the classification references. The number of peaks and/or degree of disturbance accurately capture the anomalous conditions of the pulse wave patterns, in other words, the trends that reflect such symptoms as arteriosclerosis, arrhythmia and heart disease.

It is also preferable to provide in the pattern classification means, a means (1025) for detecting the peak widths of the said pulse wave patterns and to perform the classification (1026) of pulse wave patterns using the peak widths as a part of the classification references. The peak widths reflect, in particular, conditions of the blood vessel including anomalies of the expandability of the blood vessel due to arteriosclerosis, fatigue caused by stress, tension, etc.

Furthermore, it is preferable to equip a blood pressure detection means (25) that detects at least the systolic pressure on the basis of the pulse wave component or the pulse wave pattern and to arrange so that the pulse wave pattern classification (1027, 1029) is performed at the pattern classification means by the use of the systolic pressure detected by the blood pressure detection means as a part of the classification references. Although there are cases wherein the classification of wave pulse patterns cannot be performed only by the shapes of the patterns, the use of the blood pressure value as part of the classification references enables classification from a comprehensive standpoint.

BRIEF DESCRIPTION OF THE DRAWINGS

FIG. 9 is an explanatory diagram that shows typical examples (patterns A, B, C, D and E) and measured examples of pulse wave patterns and the corresponding symptoms.

FIG. 11 is a graph that shows patterns before and after errors in the pulse wave amplitude, that were caused by body movement, etc., have been removed.

FIG. 12 is a graph for explaining the data interpolation and filtering (smoothing) processes.

A PREFERRED EMBODIMENT OF THE INVENTION

An embodiment of an electronic blood pressure measuring device by the present invention shall now be described with reference to the drawings. The measuring device in the present embodiment is one which premises the derivation of pulse wave amplitudes by the oscillometric method and one in which blood pressure measurements by the oscillometric method can be carried out simultaneously. Before describing the measuring device itself, the measurement principles of the measuring device and the relationship between the measurement principles and the internal bodily factors shall be described.

The transmural pressure (the difference between the internal pressure and the outer pressure) of the blood vessel and the variation in the blood vessel volume caused by the transmural pressure determine the minute pulse wave amplitudes which are overlaid onto the cuff pressure during the process of gradually decreasing or increasing the cuff pressure. The present inventors have found that a large non-linearity exists between the elastic modulus of the blood vessel and the transmural pressure as shown by the solid line in FIG. 5. The variation of the blood vessel volume increases rapidly at parts where the transmural pressure is small and the expandability of the blood vessel is the largest when the blood pressure and the internal pressure are approximately equal, that is, when the applied cuff pressure is nearly equal to the mean blood pressure.

Thus, pulse waves are not observed when the applied cuff pressure is high enough to overcome the systolic pressure at the start of the gradual pressure decreasing process and a pulse wave $1b$, with a small amplitude, results from pulse $1a$ and is detected only after the cuff pressure decreases somewhat. When the cuff pressure decreases further, a pulse wave $2b$, with a larger amplitude, is obtained as a result of pulse $2a$ and when the cuff pressure becomes equal to the mean blood pressure, a pulse wave $3b$, with the maximum amplitude, is generated as a result of pulse $3a$. As the cuff pressure decreases further, the amplitude of the pulse wave decreases ($4a$, $4b$) and in the final stage wherein the variation in expandability is small, pulse waves with small amplitudes ($5a$, $5b$) are obtained.

Figure 5:
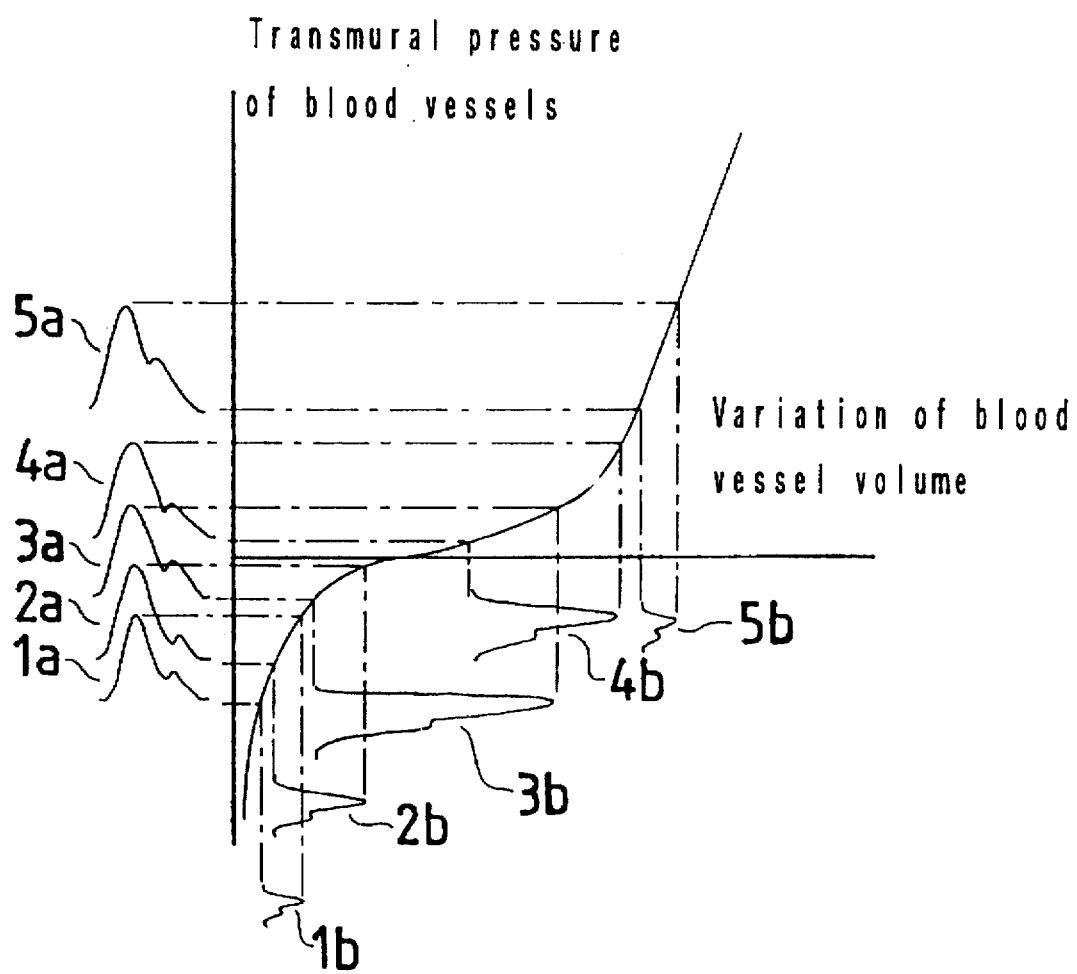
FIG. 5 is a graph that shows the relationship between the transmural pressure (the difference between the internal pressure and the outer pressure) and the variation of the volume of a blood vessel.
Figure 6:
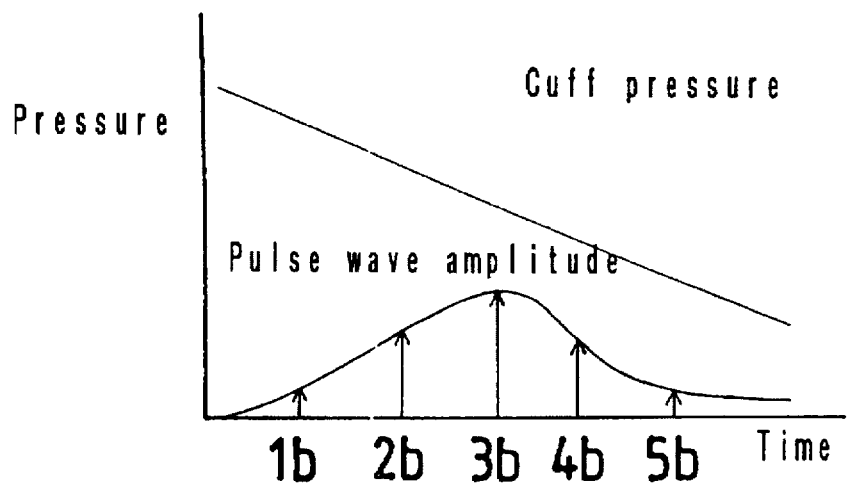
FIG. 6 is a graph that shows a comparison of the variations in time of the cuff pressure and of the pulse wave amplitude.

As shown in FIG. 5, the expandability of the blood vessel is the basic factor behind why a characteristic pulse wave amplitude pattern is obtained by a sphygmomanometer. FIG. 6 shows the relationships of correspondence between the cuff pressure and the detected pulse wave amplitude. The pulse wave amplitude pattern derived from the decreasing process of the cuff pressure is thus a result of the non-linear property (variation in elastic modulus) of the blood vessel shown in FIG. 5 and this non-linear property results from the blood vessel structure and the variations thereof. That is, a blood vessel is constituted of elastic fibers formed from muscle tissue and of collagenous fibers of a low expandability that surround the elastic fibers. Thus, when the internal pressure applied to the blood vessel is low, the tension of the vascular wall is mainly supported by the elastic fibers and the blood vessel exhibits a large expandability. On the other hand, when the blood vessel is expanded, the blood vessel exhibits a small expandability due to the restriction of the deformation of the blood vessel by the collagenous fibers.

Figure 7:
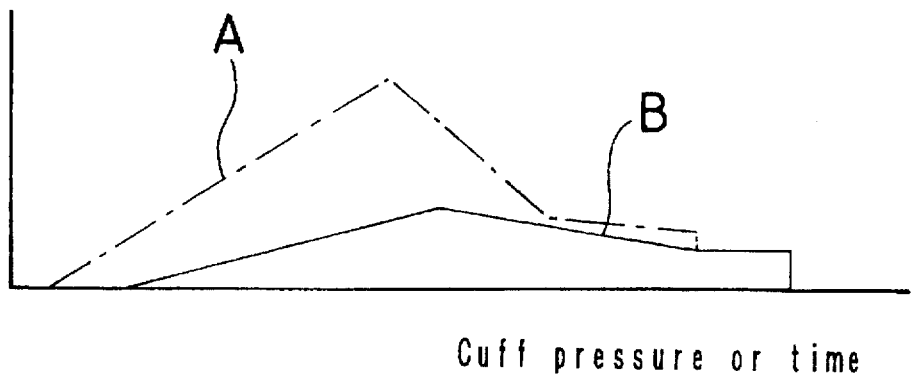
FIG. 7 is a graph that shows typical examples of pulse wave patterns (pattern A and pattern B).
Figure 8:
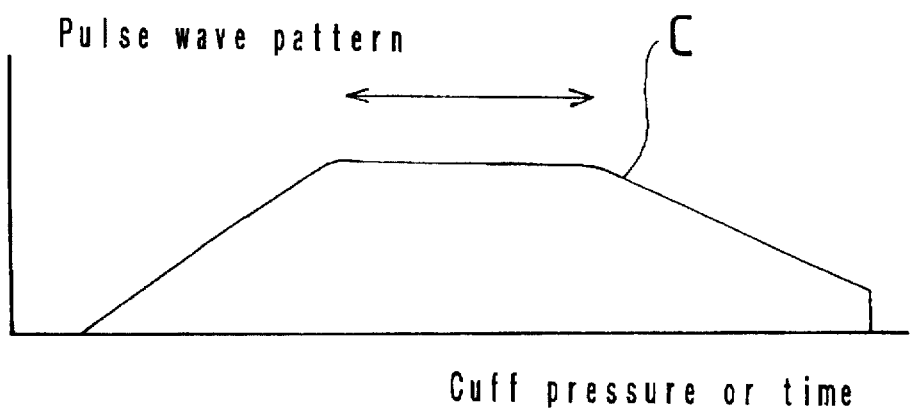
FIG. 8 is a graph that shows a typical example of a pulse wave pattern (pattern C).

The pulse wave patterns, that are obtained as a result of the characteristics shown in FIG. 5, actually take on various shapes that depend on the amount of the pressure variation caused by pulses and the conditions of the blood vessel. The pulse wave amplitudes of a pulse wave pattern become large when the expandability of the blood vessel is large and when the cardiac output is large. When a change occurs in the condition of the blood vessel, in particular, when hardening of the elastic fibers occurs, changes occur in the expansion characteristics of the blood vessel, shown in FIG. 5, that lead to changes in the shape of the pulse wave pattern (especially the peak shape). FIG. 7 shows, in comparison, a pattern A that is obtained when the circulatory system is normal and a pattern B that is obtained under conditions of hypotension, anemia or shock. FIG. 8 shows a pattern C, which appears characteristically when a sclerosing lesion or a strong tension exists at the blood vessel. Although it is often thought in such cases that the pulse wave amplitude will decrease since the elastic modulus of the blood vessel usually rises due to the lesion or tension, since these are generally accompanied by increases in the vascular resistance which leads to a rise in the blood pressure and in the pulse pressure, the size of the pulse wave amplitude will not decrease necessarily.

Figure 3:
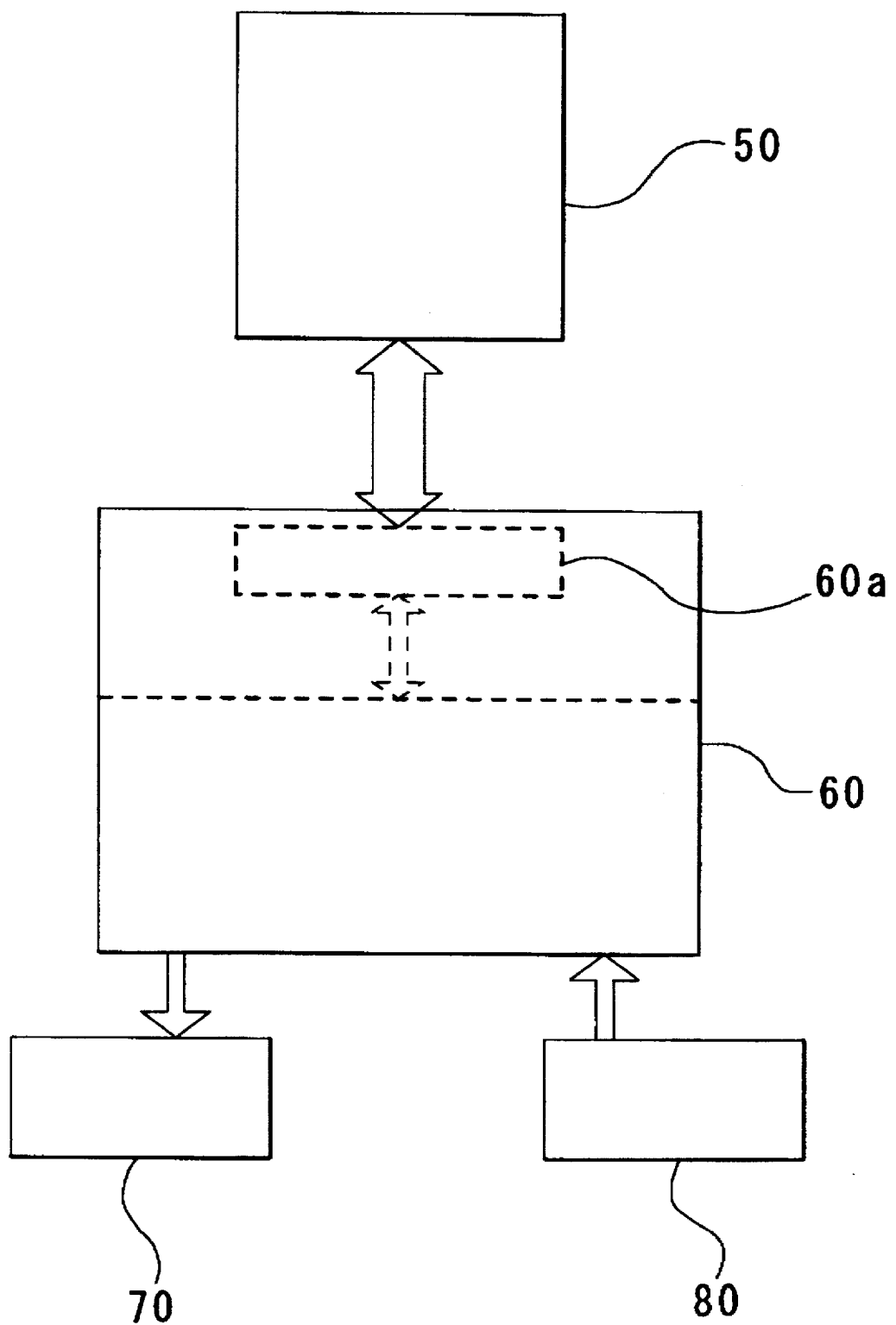
FIG. 3 is an outline block diagram which shows the overall arrangement of an embodiment by the present invention.

The arrangement of the present embodiment that was arranged based on the above knowledge shall be described next. As shown in FIG. 3, the present embodiment is comprised of a sphygmomanometer unit 50, which is connected to a cuff (arm band) and which detects the pulse wave from the measured cuff pressure for the determination of the blood pressure, a personal computer 60, which controls said sphygmomanometer unit 50 and which receives and processes the data measured by sphygmomanometer unit 50, an output device 70, such as a display, printer or plotter, that is connected to personal computer 60 and an input device 80, such as a keyboard, mouse or operation switch.

Figure 1:
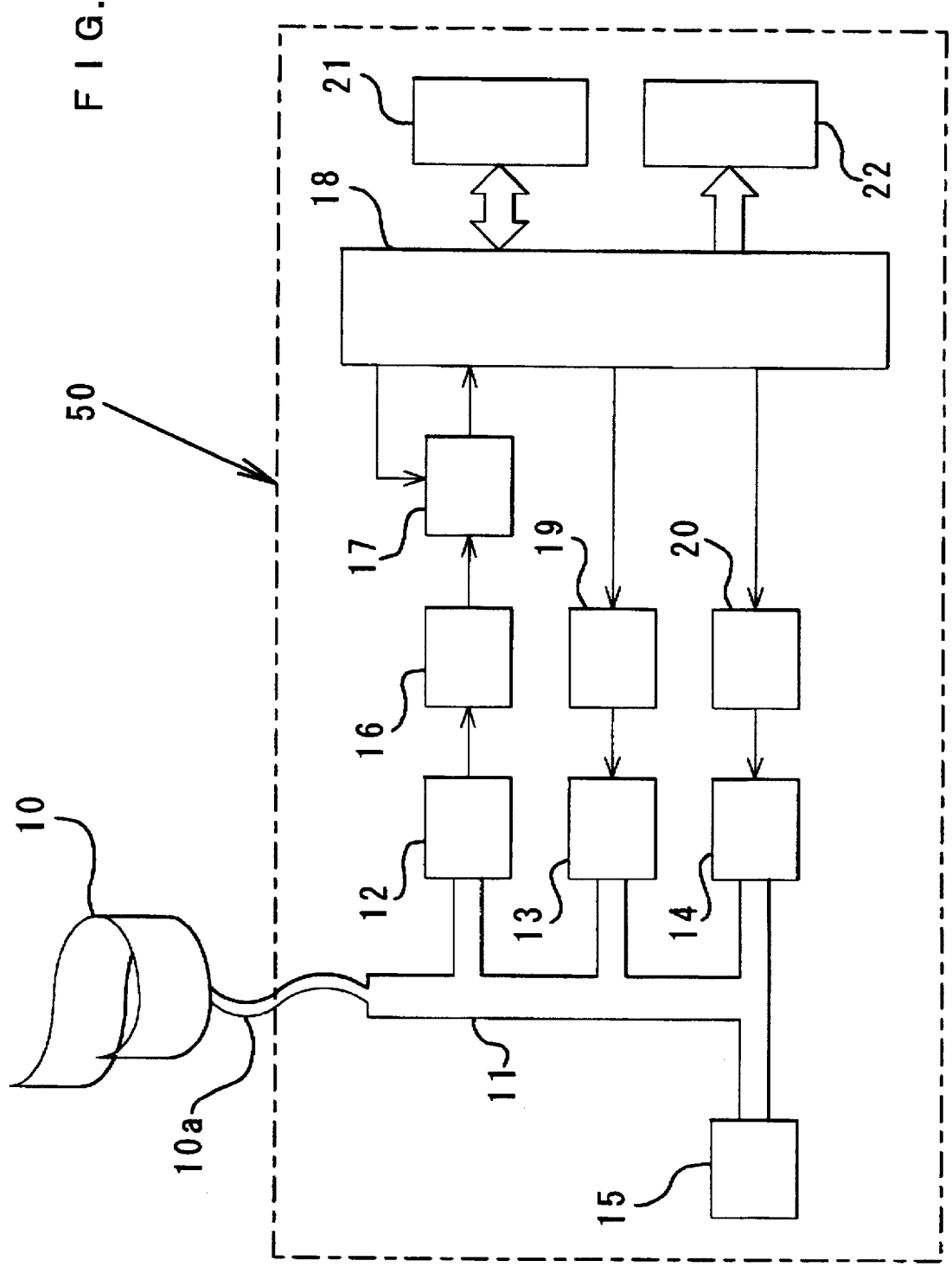
FIG. 1 is a block diagram which shows the arrangement of a sphygmomanometer in the embodiment of an electronic blood pressure measurement device by the present invention.

FIG. 1 shows the structural blocks of the sphygmomanometer 50 of the present embodiment. A capacitance type pressure sensor 12, a forced exhaust valve 13, an air compressor pump 14 and a gradual exhaust valve 15 are connected to an internal piping 11 which is in turn connected to a flexible tube $10a$ of cuff 10. Pressure sensor 12 is connected to a capacitance-frequency conversion circuit 16 which transmits the pressure detection signal of a frequency that corresponds to the cuff pressure. The number of pressure detection signals for each predetermined time interval is counted by a gated counting circuit 17 and the counts are inputted into MPU (microprocessor unit) 18.

At each predetermined time interval, MPU 18 transmits an input control signal to gated counting circuit 17. Forced exhaust valve 13 is actuated by the turning on and off of a solenoid and is driven via forced exhaust valve driving circuit 19 by control signals from MPU 18. Air compressor pump 14 is a small rolling pump and is driven via pump driving circuit 20 by control signals from MPU 18.

Figure 2:
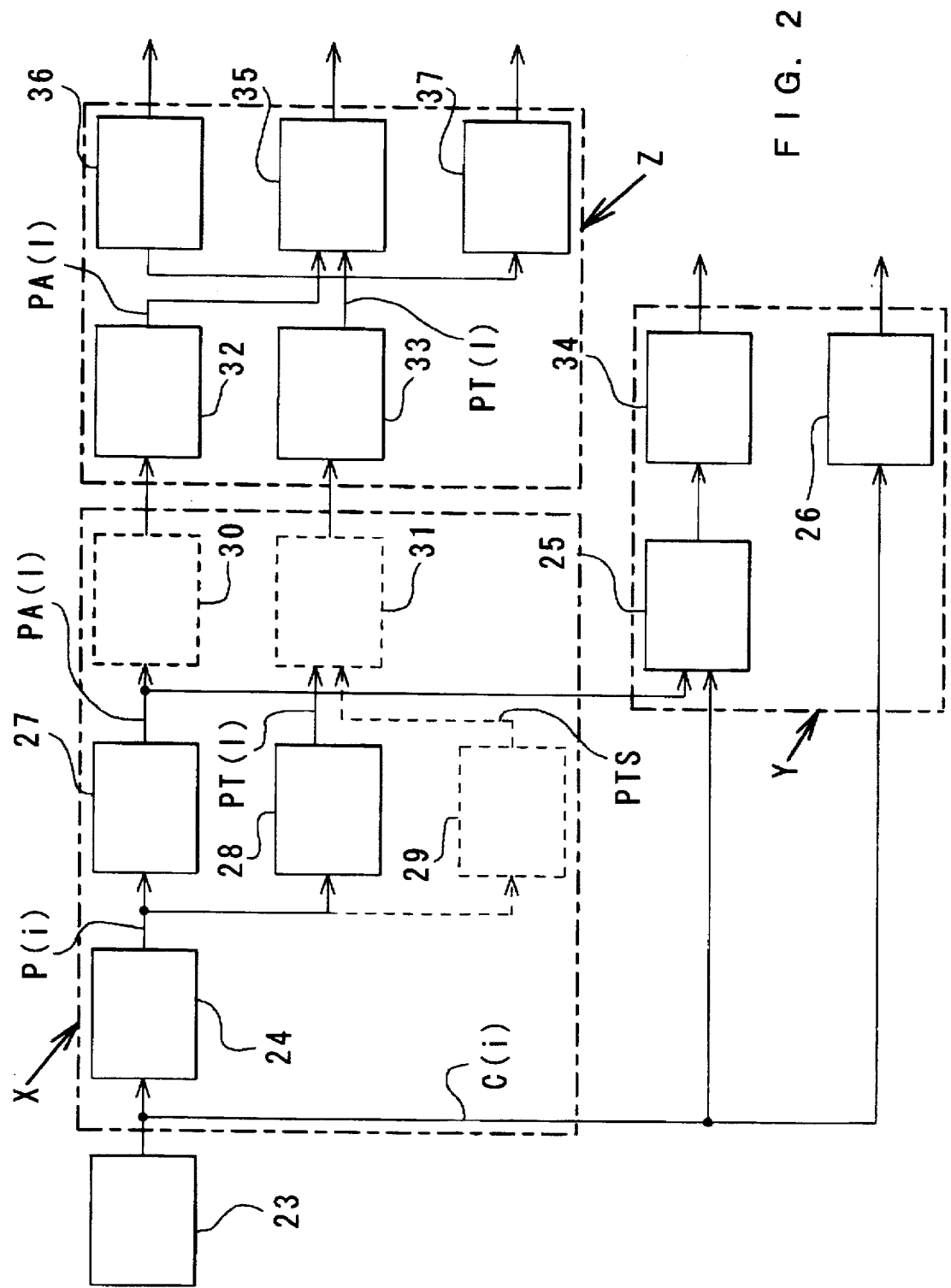
FIG. 2 is a functional block diagram which shows the processes, carried out in said embodiment, as a combination of means of implementation of the functions.

A communication interface circuit 21, that inputs and outputs measured data and control codes, and an output circuit 22, for directly outputting data to an external storage device, etc., are connected to MPU 18. Communication interface circuit 21 is connected to input/output circuit part $60a$ of the personal computer 60 shown in FIG. 3. FIG. 2 shows, in a functional manner, the means that are mainly realized by software inside MPU 18 and personal computer 60. The cuff pressure detection means 23, shown in FIG. 1 and comprising pressure sensor 12, capacitance-frequency conversion circuit 16 and gated counting circuit 17, transmits the cuff pressure value $C(i)$ shown in FIG. $4(a)$, for example, at 50 msec intervals to pulse wave signal extraction means 24, blood pressure judging means 25 and cuff pressure storage means 26.

Of the cuff pressure values that are sequentially obtained from cuff pressure detection means 23, a predesignated number (for example, 5) of the latest cuff pressure values (for example, $C(i-4)$, $C(i-3)$, $C(i-2)$, $C(i-1)$ and $C(i)$) are stored in a constantly renewed manner by pulse wave signal extraction device 24. The difference, between the latest cuff pressure value $C(i)$ and the cuff pressure value $C(i-4)$ preceding the latest value by the predesignated number, is then calculated to determine the difference signal $d(i)$, shown in FIG. $4(b)$. Thereafter, the pulse wave component signal $P(i)$, shown in FIG. $4(c)$, is computed by eliminating from said difference signal $d(i)$, the influence of the average amount of pressure decrease that is calculated from a plurality of cuff pressure values $C(i)$ obtained within a predetermined time (for example, 1 second). Besides using such a method to obtain pulse wave component signal $P(i)$, a signal equivalent to the pulse wave component signal $P(i)$ can be obtained, for example, by extracting the pulse wave signal directly from the cuff pressure value by means of a band filter and differentiating such a pulse wave signal.

The pulse wave component signal $P(i)$ is transmitted to pulse wave amplitude detection means 27, pulse wave interval detection means 28 and average interval computing means 29. Pulse wave amplitude detection means 27 cumulatively adds only those values of pulse wave component signal P(i) in the positive region for each pulse wave in order to detect the pulse wave amplitudes PA(I), shown in FIG. 4(d), and transmits the PA(I) to the pulse wave amplitude storage means 32. Pulse wave interval detection means 28 determines the time, for example, at which the pulse wave component signal P(i) changes from being positive to being negative, for each period to detect the time interval PT(I) of the pulse wave component on the basis of such a time and transmits the time interval PT(I) to the pulse wave interval storage means 33. In this case, instead of determining the time interval, the sampling number of cuff pressure values that corresponds to the time interval or the interval of the value of the cuff pressure value C(i) that corresponds to each time, in other words, the pressure interval, can be detected and used as the time interval PT(I).

An average interval computing means 29, an amplitude quantization means 30 and an interval quantization means 30 may be provided to lighten the data load to be stored by the said pulse wave amplitude storage means 32 and pulse wave interval storage means 33. Average interval computing means 29 computes the average value of the pulse wave periods in pulse wave component signal P(i) and transmits the value, obtained by accumulating a predetermined number of pulse wave intervals (for example, the 6 pulse wave intervals computed immediately after the start of measurement) and dividing with the predetermined number, as the average interval PTS to interval quantization means 31. In the case wherein sampling numbers or pressure intervals are detected by pulse wave interval detection means 29 as mentioned above, average interval computing means 29 detects the sampling number or the average pressure interval that correspond to the average time interval.

At interval quantization means 31, the pulse wave intervals PT(I) are compared with average interval PTS and are associated with a number of interval sections to reduce the amount of data. For example, if PT(I)>2PTS then N(I)=3, if 2PTS>PT(I)>1.5PTS then N(I)=2, if 1.5PTS>PT(I)>0.5 PTS then N(I)=1 and if 0.5PTS>PT(I) then N(I)=0, where N(I) is the quantized pulse wave interval.

The pulse wave amplitude PA(I) that is outputted by the said pulse wave amplitude detection means 27 may also be converted to a quantized amplitude value by the association of each pulse wave amplitude PA(I) with a number of amplitude sections by means of amplitude quantization means 30. The interval and amplitude quantization means 30 and 31 reduce the load in terms of volume and time of subsequent data processing (including data storage) by cutting off the unnecessary resolution of the detected value. The resolution of the data after quantization is set as appropriate according to the detection accuracy required. Obviously, if there are no problems in the load in terms of volume and time, the said quantization means are unnecessary.

The pulse wave amplitudes PA(I) are inputted along with the cuff pressures C(i) into blood pressure judging means 25 and the systolic pressure Pmax, the diastolic pressure Pmin, the mean blood pressure Pave, the pulse rate, etc. are computed by real time processing. For example, the mean blood pressure Pave is determined as the cuff pressure C(imax) at the point at which the maximum value PA(Imax) of the pulse wave amplitudes PA(I) was obtained, the systolic pressure Pmax is determined as the cuff pressure C(is) at the point at which a pulse wave amplitude PA(Is), corresponding to a predetermined percentage S % of the maximum value PA(Imax), was obtained at the higher pressure side of the point at which PA(Imax) was obtained, and the diastolic pressure Pmin is determined as the cuff pressure C(id) at the point at which a pulse wave amplitude PA(Id), corresponding to a predetermined percentage D % of the maximum value PA(Imax), was obtained at the lower pressure side of the point at which PA(Imax) was obtained. In other words:

$$PA(Imax) \times S/100 = PA(Is)$$
$$PA(Imax) \times D/100 = PA(Id)$$

The output of blood pressure judging means 25 is inputted into blood pressure storage means 34 which stores the blood pressure values. For example, the addresses of the data stored in pulse wave amplitude storage means 32 and cuff pressure storage means 26 are stored.

The said procedures of each means are carried out in real time and the measurement is completed when the diastolic pressure is judged. Thereafter, processes such as the display of the blood pressure and the classification of the pattern are carried out on the basis of data stored in storage means 26, 32, 33 and 34. Of the functional blocks shown in FIG. 2, the data processing part X and the blood pressure computing part Y are executed by MPU 18 within sphygmomanometer unit 50 and the pattern judging part Z, that shall be described later, is executed by the personal computer 60 shown in FIG. 3.

The actual operation of MPU 18 is started by the start command which is transmitted from personal computer 60 as a result of an input from input device 80. By the start command, MPU 18 closes forced exhaust valve 13, starts up air compressor pump 14 and raises the pressure within cuff 10 to a preset pressure setting (for example, 140 mmHg). It is possible to preset the initial value of the pressure setting and if the pressure is not sufficient, recompression is performed by automatically increasing the pressure in up to 2 stages and by 30 mmHg per stage. When the pressure of the interior of cuff 10 is raised to the pressure setting, air compressor pump 14 is stopped and the sampling of the measured pressure values is started. Gradual exhaust valve 15 reduces the pressure within cuff 10 at a rate of approx. 3~6 mEg/second. The cuff pressure values are sampled in intervals of approx. 50 msec and upon each sampling, counting circuit 17 takes in the pressure detection signal of capacitance-frequency conversion circuit 16 for approximately 8.2 msec and counts the number of incoming pulses during this time. Such sampling of measured values is continued in parallel with the computation of the mean blood pressure, the systolic pressure and the diastolic pressure and the measurement ends at the point at which the diastolic pressure is obtained.

The pulse wave amplitudes PA(I), that are stored in the said pulse wave amplitude storage means 32, and the pulse wave intervals PT(I), that are stored in the said pulse wave interval storage means 33, are inputted into pulse wave pattern generation means 35 and, if necessary, pulse wave patterns, that are suited for the pattern comparison operation, are generated according to the reference values in reference value storage means 36 and are outputted to output device 70 and transmitted to pulse wave pattern classification means 37. Reference value storage means 36 usually stores and holds a number of typical examples of pulse wave patterns, in other words, reference patterns and, if necessary, also stores the scale of the reference pattern and other reference values that indicate the characteristics of the reference pattern.

The pulse wave pattern classification means 37 compares the pulse wave pattern generated by pulse wave pattern generation means 35 with a plurality of reference patterns stored by reference pattern storage means 36 and classifies the pulse wave pattern as one of the reference patterns. Besides the method to be described later in which the pulse wave pattern and reference patterns are compared by direct comparison of entire patterns, methods may be used in which the classification is performed by using reference values extracted from the reference pattern as classification references or in which the classification is performed by detecting peak widths and number of peaks (classification references for patterns A, C and E shown in FIG. 9), intervals of peak amplitudes (classification reference for patterns A and D shown in FIG. 9), etc. on the basis of reference values stored in advance in a storage means.

FIG. 9 shows 5 pulse wave pattern types, A to E, as typical examples of pulse wave patterns. A reference pattern, a pulse wave pattern that corresponds to each reference pattern and clinical cases that are thought to correspond to each reference pattern are shown for each type. These reference patterns are stored in the later mentioned reference pattern storage means 36 as typical examples that were extracted from statistical processing of a large number of cases. It is also possible, for example, to add modifications to the said plurality of reference patterns on the basis of pulse wave patterns of normal conditions that are registered according to each individual in order to reduce the influence of individual differences on the judgement.

Figure 4:
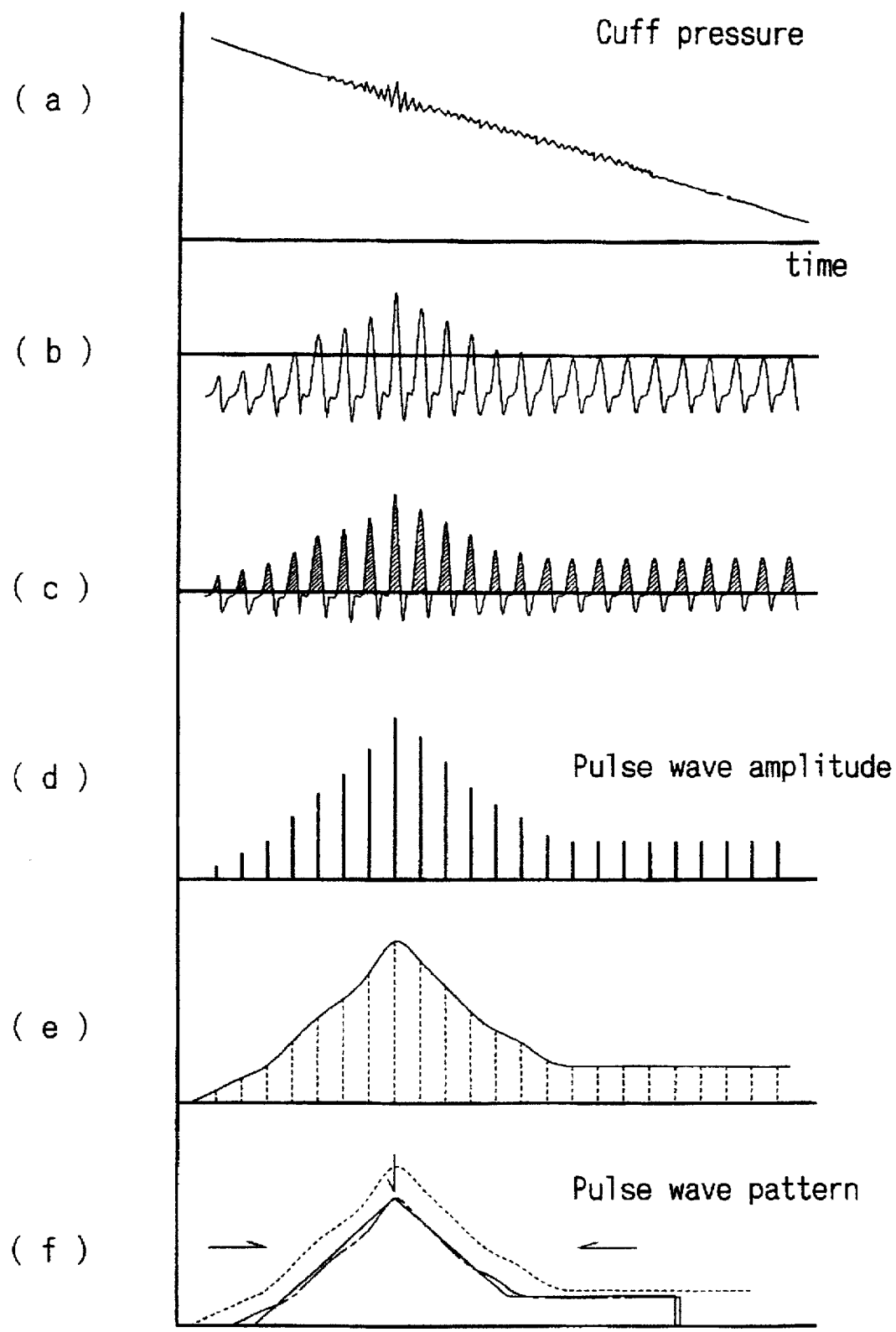
FIG. 4 is a timing chart which shows the signal forms of the processes carried out by the MPU in the said embodiment.
Figure 10:
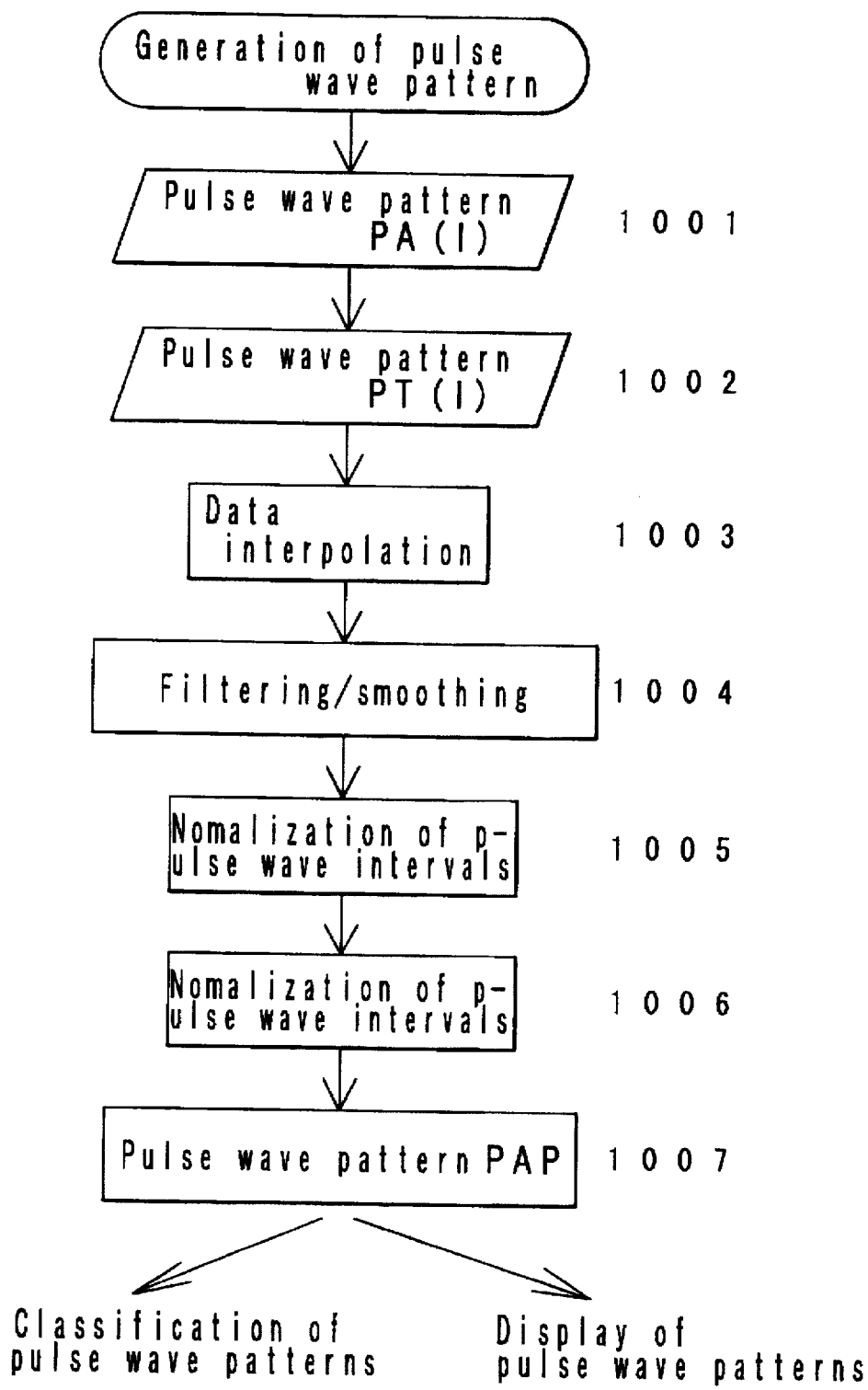
FIG. 10 is a flowchart that shows the pattern generation procedure carried out by the pulse wave pattern generation means.

FIG. 10 shows the processing procedure that is carried out at pulse wave pattern generation means 35. First, the pulse wave amplitudes PA(I) and the pulse wave intervals PT(I) are read in (1001, 1002) and the pulse wave amplitudes PA(S) (S is the sample number), shown in FIG. 4(e), are determined by interpolating the interval between the values of each pulse wave amplitude PA(I) by a straight line or a sine curve (1003). Here, the maximum sample number S is the number of data required to improve the display conditions and to secure the required amount of information for the pattern classification to be described later. In this case, the sample number S may, for example, be set equal to the sampling number i of the cuff pressure detection data. Next, the pulse wave amplitudes PA(S) are smoothed by calculating simple averages:

$$\{P(S-1)+P(S)+P(S+1)\}/3 \rightarrow P(S)$$

or weighted averages:

$$\{P(S-1)+2P(S)+P(S+1)\}/4 \rightarrow P(S)$$

or moving averages (1004). Such processes for data interpolation and filtering/smoothing are expressed visually in FIG. 12. Here, it is preferable to perform the prior process shown in FIG. 11 before performing the data interpolation process shown in FIG. 12. This is because large measurement errors, such as PA(Ie)=Pe, may arise in the pulse wave amplitudes PA(I) due to movement of the body by the subject during the measurement. Such erroneous data should be eliminated prior to data interpolation and filtering/smoothing since such data will bring about a bad effect on the subsequent processes. This process is performed when a difference that is no less than a predetermined amount or a predetermined percentage arises between PA(I) and a reference value computed from the data prior and subsequent to PA(I).

For example, the value of PA(I) is compared to a reference value (for example an average, a moving average, etc.) calculated from n prior data and n subsequent data (for example, if n=3, the 6 data of PA(I-3), PA(I-2), PA(I-1), PA(I+1), PA(I+2), PA(I+3)) and if the difference between the measured data and the reference value exceeds a predetermined value (for example, if the difference is 30% or more of the reference value), the measured value is judged to be an outlying data and, as shown in the graph at the bottom of FIG. 12, the measured data Pe is replaced by reference value Pc. In the case of data at both ends, for which the reference value for PA(I) cannot be calculated, in other words in the case $I \leq n$ or $I \geq Im-n+1$ (Im is the number of pulse wave amplitude data), the reference value may be calculated by decreasing the number n or the amplitude data in the range, $I \leq n$ and $I \geq Im-n+1$, may be eliminated and such parts at both ends may be removed from being subjected to subsequent processes.

Figure 13:
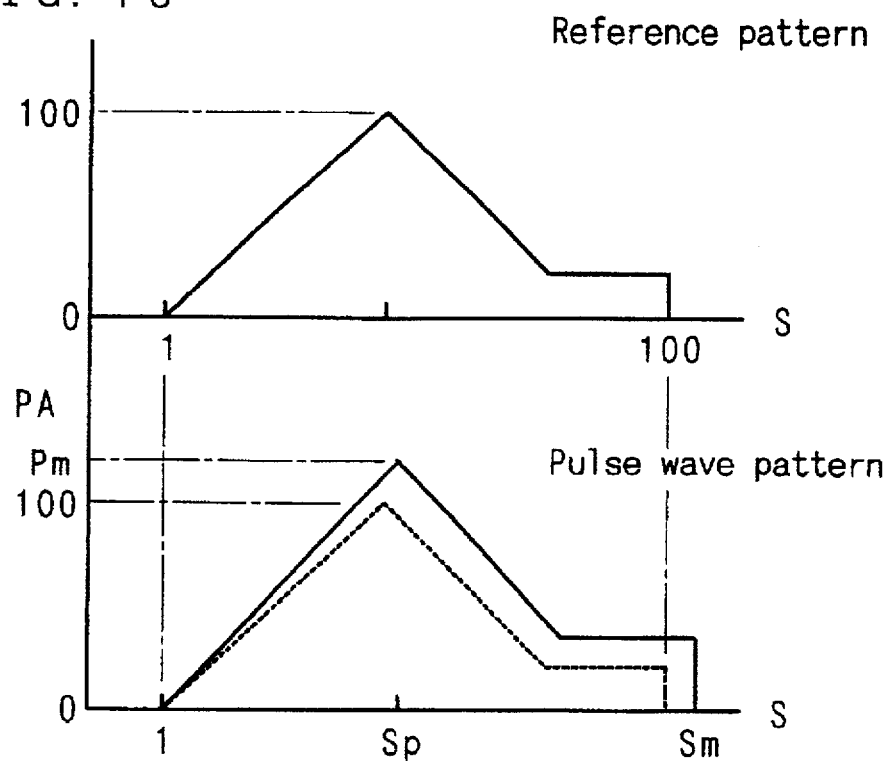
FIG. 13 is a graph for explaining the process of normalization of pulse wave patterns.

After the filtering/smoothing process, the normalization of the pulse wave interval and the normalization of the pulse wave amplitude are performed as indicated by 1005 and 1006 in FIG. 10. In this case, if the normalization constants for the pulse wave interval and pulse wave amplitude are both set to 100, as shown in FIG. 13, the maximum sample number Sm and the maximum amplitude Pm of pulse wave pattern PA(S) is determined and sample number S is multiplied by (100/Sm) and pulse wave amplitude PA(S) is multiplied by (100/Pm) to obtain the pulse wave pattern PAP, which is normalized to a maximum sample number of 100 and a maximum amplitude of 100 and is shown by the dotted line in the diagram. This is also shown in FIG. 4(f). Here, the normalization constant matches the maximum sample number and maximum amplitude of the reference pattern shown in FIG. 13 and by comparing pulse wave pattern PAP to the reference pattern, the differences in shape can be determined accurately. The reference pattern is stored in reference value storage means 36, for example, by storing the coordinates of the plurality of points of the envelope of the pattern and the interval between points may interpolated by a straight line or sine curve, etc. when carrying out the classification procedure to be described later. The said normalization constant may be read out as a reference value from reference value storage means 36 upon performing the normalization process (1005, 1006). The pulse wave pattern PAP is outputted to output device 70 from personal computer 60 and, for example, is displayed on a display and becomes the data subjected to the pattern classification process described below.

The said normalization of measured data is performed to facilitate the classification by comparison of the reference pattern with the pulse wave pattern (this includes both the classification procedure described below and the case in which the physician diagnoses a pulse wave pattern that is simply displayed on a display or a printer). This is because various alterations may arise in the pulse wave pattern actually measured due to such factors as the amount of subcutaneous fat of the patient, the attachment condition of the cuff and the time of measurement (day, noon, night, etc.) and because, in the case of gradual exhaust valves in which the usual rate control is not performed, the measurement speed may vary due to variations in the rate of reduction of the cuff pressure.

Figure 14:
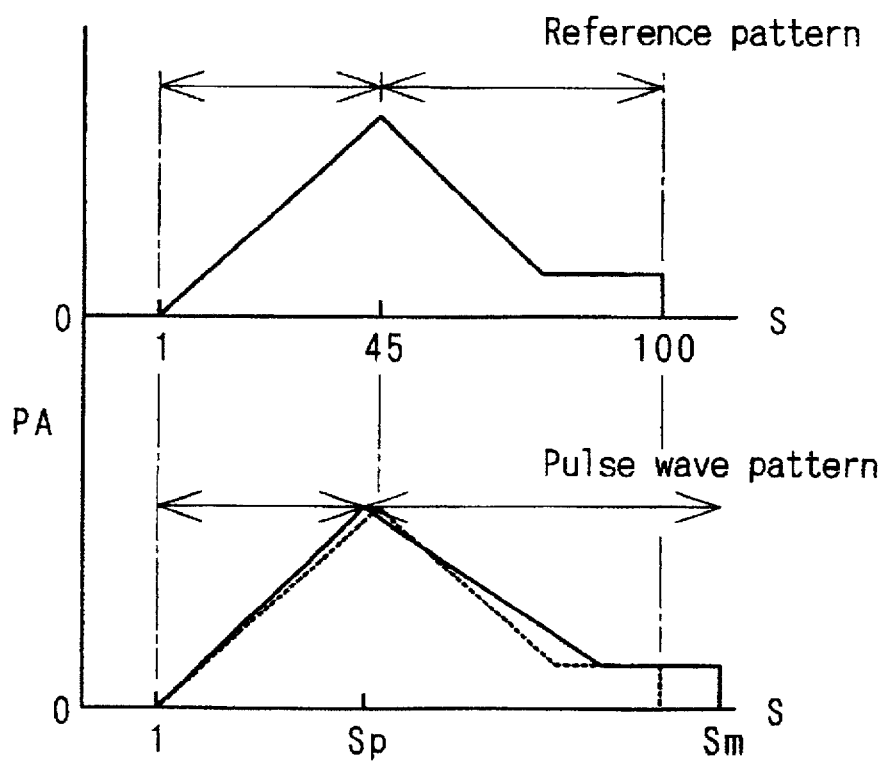
FIG. 14 is a graph for explaining a different method of normalization.

In particular, a case may arise wherein the peak value Pm appears at different positions in the reference pattern and the measured pulse wave pattern. This may occur since the mean blood pressure and elastic modulus of the blood vessel differ widely for different subjects. In such a case, the normalization of the pulse wave interval, shown in FIG. 14, is performed. In this process, the position Sp, at which the peak value appears (PA(Sp)=Pm), is used as a basis to normalize each of the sections 1~Sp and Sp~Sm with respect to the reference pattern. For example, as shown in FIG. 14, if the width corresponding to section 1~Sp of the reference pattern is assumed to be 44 and the width corresponding to section Sp~Sm of the reference pattern is assumed to be 55, the following calculation is performed on the original sample numbers S of the measured pulse wave pattern:
in the range $1 \leq S < Sp$, $$S' = (44/Sp) \cdot S$$

and in the range $Sp \leq S \leq Sm$, $$S' = \{55/(Sm-Sp)\} \cdot (S-Sp) + 45$$

The peak position of the pulse wave pattern PA(S'), shown by the dotted line in FIG. 14, is thus matched with that of the reference pattern and errors in the classification due to deviations in the peak position may therefore be prevented in the classification procedure described later.

Figure 15:
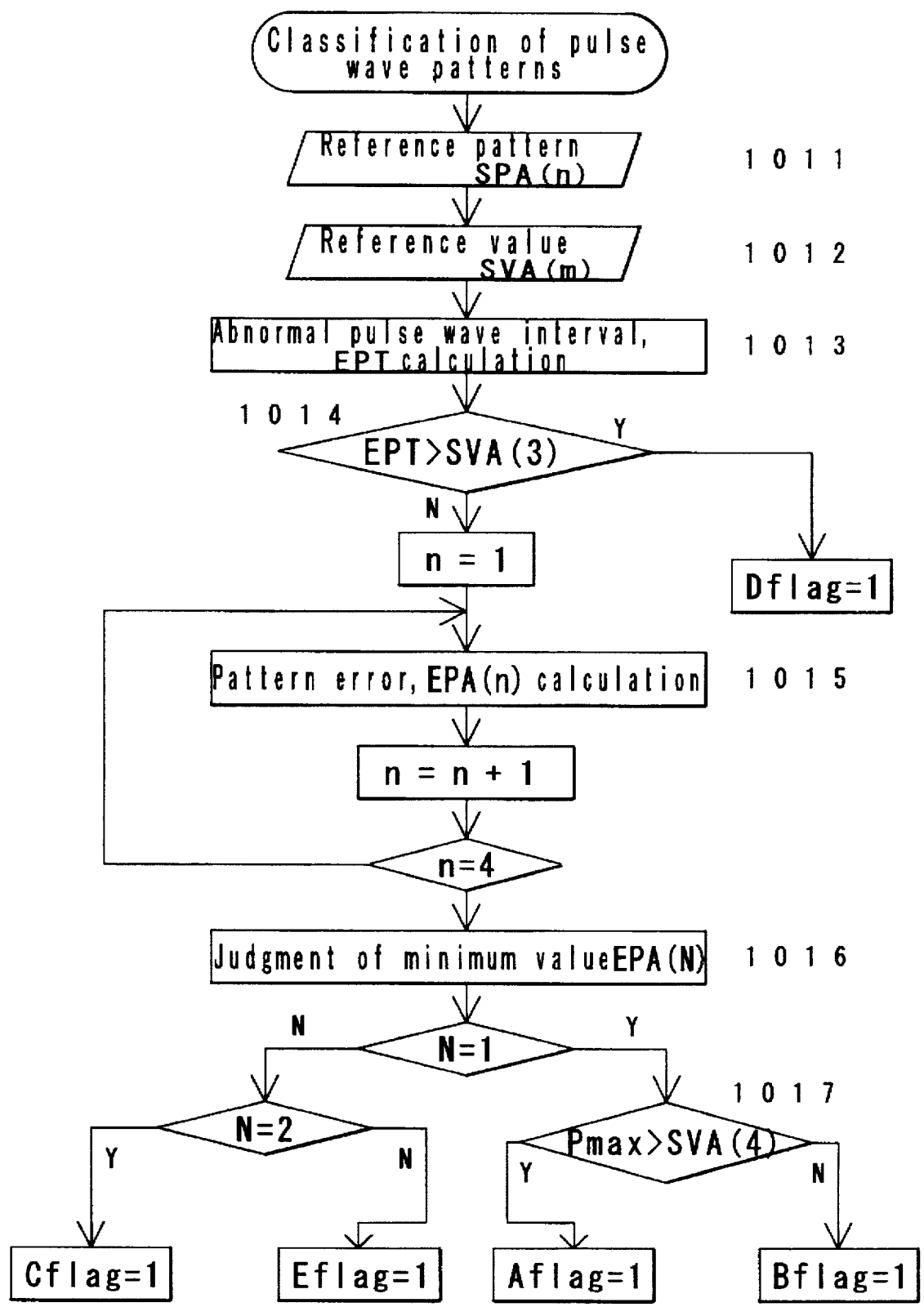
FIG. 15 is a flowchart which shows the pattern classification procedure of the pulse wave pattern classification means.

The processing procedure performed at pulse wave pattern classification means 37 shall be described next. As shown in FIG. 15, the reference patterns SPA(n) and the reference values SVA(m) are read in from reference value storage means 36 (1011, 1012). Here, the entire reference pattern SPA(n) is normalized by the said normalization constant. Next, the outlying factor EPT for the pulse wave intervals PT(I) is computed (1013). The outlying factor EPT is the number of I's for which the condition SVA(1)>PT(I)/PT(I−1)>SVA(2) is not satisfied and the values of SVA(1) and SVA(2), which stipulate the upper and lower limits respectively, are determined from statistical data. Arrhythmia may be presumed in cases wherein the ratio of sequential pulse wave intervals PT(I)/PT(I−1) is outside the said condition at many points. Thus, in cases wherein the outlying factor EPT is greater than reference value SVA(3), the pulse wave pattern is classified as pattern D, shown in FIG. 9 (1014). The reference value SVA(3) is also determined appropriately from statistical data.

If outlying factor EPT is less than reference value SVA(3), the pulse wave pattern PAP is compared with reference patterns SPA(n) (1015). The reference pattern SPA(n) is that which corresponds to pattern A or pattern B when n=1, to pattern C when n=2 and to pattern E when n=3. Here, the square of the deviations of the amplitudes of pulse wave pattern PAP and amplitudes of the respective reference patterns SPA(n) are summed over all sample numbers to compute pattern error EPA(n). That is, $$EPA(n) = \sum_{S=1}^{Sm} \{PA(S) - SPA(S, n)\}^2$$

The correlation between pulse wave pattern PAP and reference pattern SPA(n) may also be determined from the summation of deviations and other methods.

Next, the least of the pattern errors EPA(n) is judged (1016) and set as EPA(N). If N=1 and if the maximum value Pm of the pulse wave amplitudes (the maximum amplitude before normalization) is greater than a reference value SVA(4), a flag is placed on pattern A while if Pm is less than SVA(4), a flag is placed on pattern B. If N=2, a flag is placed on pattern C and if N=3, a flag is placed on pattern E. The said reference patterns SPA(n) and reference values SVA(m) should be set appropriately and statistically on the basis of numerous measurement examples and it is preferable to be able to modify these appropriately for a specific individual when necessary.

The pulse wave pattern PAP and the result of pattern classification, obtained by the method described above, are displayed at output device 70 shown in FIG. 3. This output device 70 displays the cuff pressure, the pulse wave component and the pulse wave amplitudes in real time during blood pressure measurement and simultaneously displays each of the blood pressure values, the pulse rate, the classified pattern, the pulse wave pattern itself and the plurality of reference patterns shown in FIG. 9 after the measurement.

Although the MPU 18 for blood pressure measurement and the personal computer 60 for data processing are provided separately as shown in FIG. 3 in the present embodiment, both the real time processing for blood pressure measurement and the pulse wave pattern processing may also be performed with one computing device.

By the present embodiment, the pulse wave pattern is displayed at a display or some other output device 70 and, at the same time, is classified only on the basis of the shape of the pulse wave pattern using means that use predetermined criteria, for example, normalization. Furthermore, the classification is also performed on the basis of the magnitudes of the pulse amplitudes prior to being normalized as a pulse wave pattern. By eliminating the effects of detection errors due to noise, etc. by interpolation and smoothing of the pulse wave pattern and by combining such processes with the normalization of the pattern, information on the vascular dynamics, in particular, information on the expandability of the blood vessel, can be derived regardless of measurement conditions or individual differences (differences in pulse rate, blood output, skinfold thickness, blood pressure amplitude and difference between systolic and diastolic pressures). Furthermore, the displaying of normalized pulse wave patterns enables the estimation of the reliability of blood pressure values, etc. through comparisons of patterns and enables accurate judgements that are not mislead by a simple indication of just numbers. The operation command for sphygmomanometer unit 50 is transmitted from personal computer 60 and, furthermore, the display and storage of measured data and classification patterns and the display of explanations of the operation procedure are executed under the control of personal computer 60 on the basis of inputs from input device 80.

Figure 16:
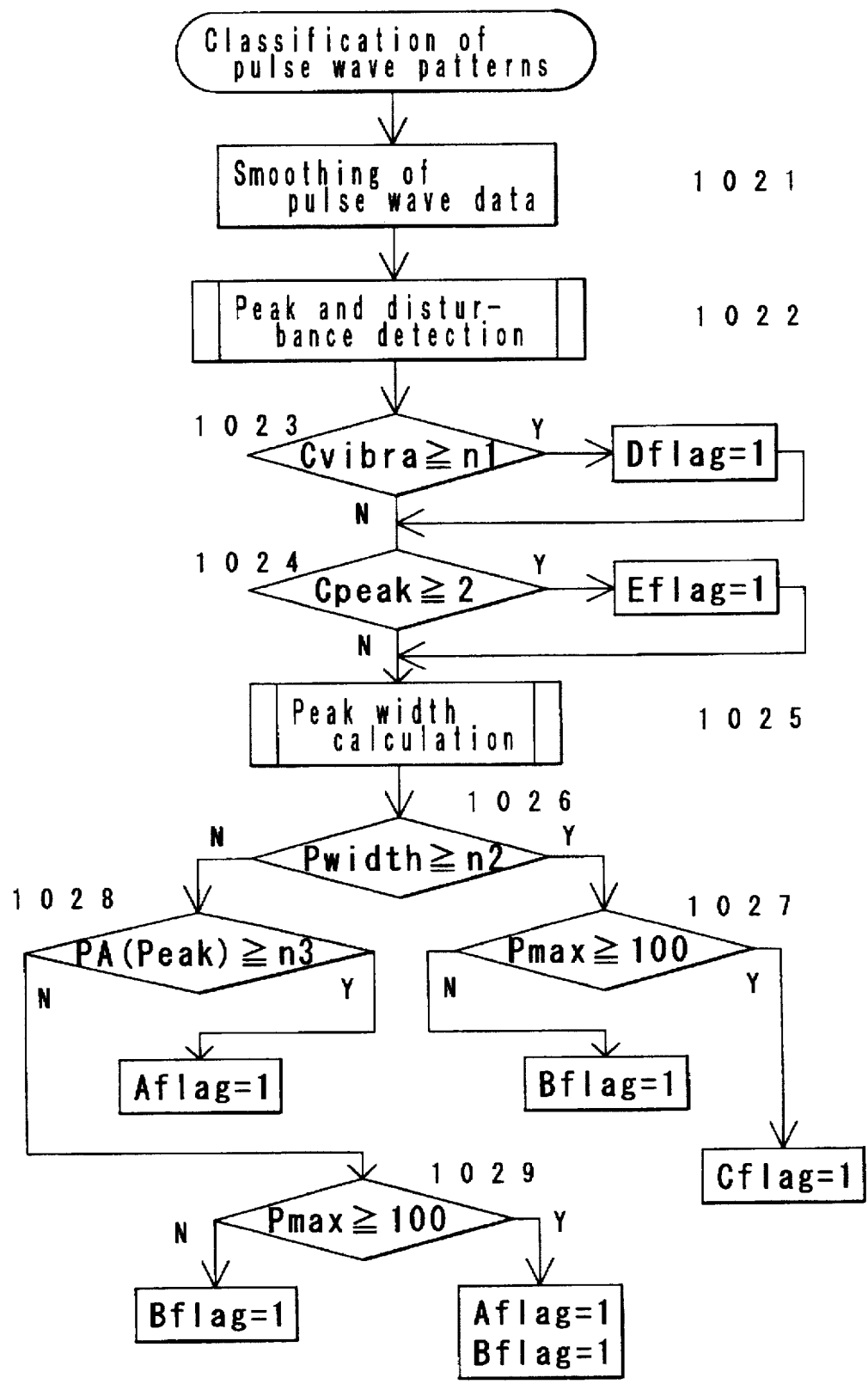
FIG. 16 is a flowchart which shows a pattern classification procedure that is different from that shown in FIG. 15.
Figure 17:
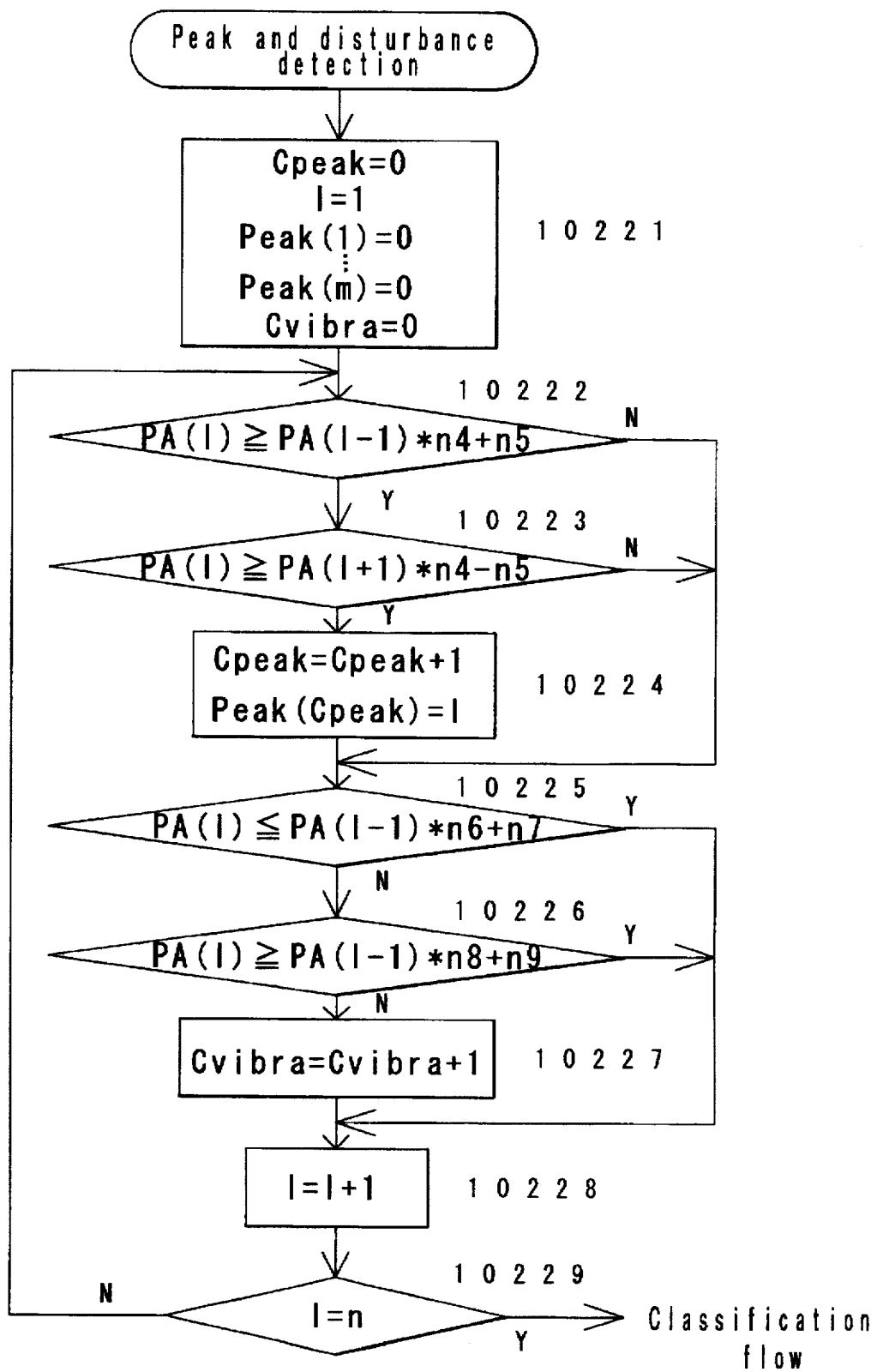
FIG. 17 is a flowchart that shows, in detail, the peak and disturbance detection procedure in the pattern classification procedure shown in FIG. 16.
Figure 18:
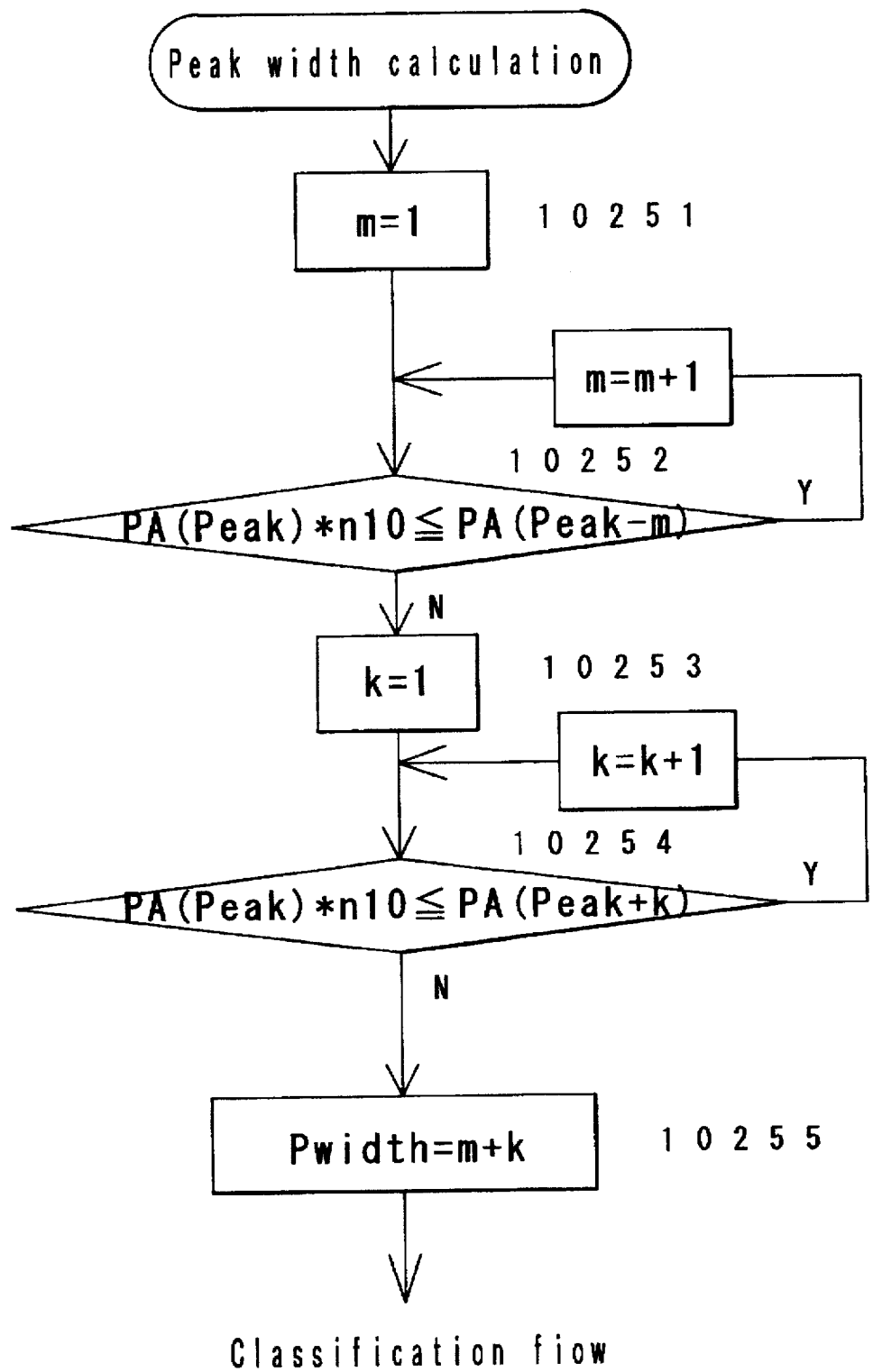
FIG. 18 is a flowchart that shows, in detail, the peak width calculation procedure in the pattern classification procedure shown in FIG. 16.

A different embodiment of the said pattern classification means 37 shall now be described with reference to FIGS. 16 to 18. FIG. 16 shows the overall structure of a classification procedure based on pulse wave patterns. Although pulse wave pattern PAP obtained through the pulse wave pattern generation procedure shown in FIG. 10 can be classified by this classification procedure, the pulse wave amplitude PA(I), shown in FIG. 3(d), is classified directly instead of normalized pattern PAP in this procedure. First, the pulse wave amplitude PA(I) is smoothed by a predetermined method (1021), for example by weighted averaging with a predetermined number of prior and subsequent data, and then the peaks and the disturbance of the smoothed pulse wave amplitude PA(I) are detected (1022). FIG. 17 shows the procedure for detecting the peaks and disturbance. First, the variable Cpeak, which expresses the number of peaks in the pattern of pulse wave amplitudes PA, the variable I, that indicates the data number of a pulse amplitude PA(I), the variables Peak(1), . . . , Peak(m) (m is the number of peaks), which indicate the position of the peaks in pulse wave pattern PA by means of data number I, and the variable Cvibra, which indicates the degree of disturbance of the pulse wave amplitudes PA(I), are initialized (10221).

Next, the Ith pulse wave data PA(I) and the immediately preceding pulse wave data PA(I−1) are compared by means of 2 parameters, n4 and n5 (10222). Here n4 is a proportionality constant slightly larger than 1 which is multiplied to the absolute value of pulse wave amplitude PA and n5 is a shift quantity which does not depend on the value of pulse wave amplitude PA. If PA(I) has increased with respect to PA(I−1) by just a predetermined amount determined from the preset values of n4 and n5, the process moves on to procedure 10223 and if not so, the process moves on to procedure 10225. In procedure 10223, pulse wave amplitudes PA(I) and PA(I+1) are compared using the same parameters n4 and n5 and if PA(I+1) has decreased with respect to PA(I) by just a predetermined amount, the process moves on to 10224 and if not so, the process moves on to procedure 10225. n4 is a constant for eliminating the noise proportional to the absolute value of wave pulse amplitude PA and n5 is a constant for eliminating the noise that is not proportional to the absolute value of pulse amplitude PA and these parameters are set appropriately to suit the data measurement system and the data processing system.

In procedure 10224, it is deemed that a pulse amplitude peak has been detected and the number of peaks Cpeak is incremented by 1 and the value of peak position peak (Cpeak) is set to I. After thus detecting whether or not the data is a peak of the pulse wave pattern, the process moves on to the procedure for detecting the degree of disturbance of the pulse wave pattern. In procedure 10225, pulse wave data PA(I) and the immediately preceding pulse wave data PA(I−1) are compared and if PA(I) has not increased with respect to PA(I−1) by or by more than a predetermined increase amount determined from parameters n6 and n7, the process moves on to procedure 10228 and if not so, the process moves on to procedure 10226. In procedure 10226, the pulse wave amplitude PA(I) and the immediately preceding amplitude PA(I−1) are compared and if PA(I) has not decreased with respect to PA(I−1) by or by more than a predetermined decrease amount determined from parameters n8 and n9, the process moves on to 10228 and if not so, the process moves on to procedure 10227. In procedure 10227, it is deemed that pulse wave amplitude PA(I) has changed largely with respect to immediately preceding data PA(I−1) and the degree of disturbance Cvibra is incremented by 1. Here, the values of n6, n7, n8 and n9 are set appropriately from statistical data.

By the above process, the presence or non-presence of a peak or disturbance at the Ith pulse wave amplitude PA(I) is judged and the process is carried out on the next (I+1)th data at procedure 10228. The detection of the number of peaks Cpeak, the peak positions Peak(Cpeak) and the degree of disturbance Cvibra of the entire pattern is thus completed when all of the pulse wave amplitudes PA(I) from I=1 to n have been processed as described above.

Thereafter, the process returns to the procedure in FIG. 16 again and degree of disturbance Cvibra and a predetermined value n1 are compared at procedure 1023 and if degree of disturbance Cvibra is equal to or greater than predetermined value n1, a flag is placed on pattern D. Next, it is judged whether or not the number of peaks Cpeak is 2 or greater and if there are 2 or more peaks, a flag is placed on pattern E.

Next, the calculation of the peak width is performed in procedure 1025. The calculation of the peak width is carried out by the procedure shown in FIG. 18 on the basis of the peak positions detected in procedure 1022. First, m is set equal to 1 in Procedure 10251 and the value of the pulse wave amplitude PA(Peak) at a peak position is compared with the pulse wave amplitude PA(Peak-m) at a position m data prior to the peak position to judge whether PA(Peak-m) is equal to or greater than the value obtained by multiplying PA(Peak) by a parameter n10. If PA(Peak-m) is equal to or greater than PA(Peak) times n10, m is incremented by 1 and procedure 10252 is carried out again. Judgements are thus performed until the judgement result at procedure 10252 becomes negative and when PA(Peak-m) becomes less than PA(Peak) times n10, the process moves on to procedure 10253. Here, n10 is a value that is usually somewhat less than 1 and is set appropriately from statistical data.

At procedure 10253, k is set equal to 1 and at procedure 10254, it is judged whether PA(Peak+k) is equal to or greater than PA(Peak) times n10. If PA(Peak+k) is equal to or greater than PA(Peak) times n10, k is incremented by 1 and the judgement in procedure 10254 is carried out again. Judgements are thus carried out until the judgement result at procedure 10254 becomes negative and when PA(Peak−k) becomes less than PA(Peak) times n10, the peak width Pwidth is determined by adding the said m and k at procedure 10255.

After determining the peak width Pwidth in the manner above, the process moves on to procedure 1026 in FIG. 16 and it is judged whether Pwidth is equal to or greater than n2. Here, parameter n2 is set appropriately according to statistical data. If peak width Pwidth is equal to or greater than n2, it is judged whether systolic pressure Pmax is equal to or greater than 100 and if systolic pressure Pmax is equal to or greater than 100, a flag is placed on pattern C while if systolic pressure Pmax is less than 100, a flag is placed on pattern B (1027). On the other hand, if peak width Pwidth is less than n2, it is judged whether the pulse wave amplitude PA(Peak) of the peak is equal to or greater than n3 (1028). Here, n3 is set appropriately according to statistical data. If peak data PA(Peak) is equal to or greater than n3, a flag is placed on pattern A and the process ends. If peak data PA(Peak) is less than n3, it is judged whether systolic pressure value Pmax is equal to or greater than 100 (1029) and if systolic pressure value Pmax is equal to or greater than 100, flags are placed on both pattern A and pattern B while if systolic pressure Pmax is less than 100, a flag is placed only on pattern B.

The classification pattern is then displayed at an output device 70 such as a display in accordance with the flag placed at each pattern in the manner described above. Thus, by the detection of the number and positions of peaks, the degree of disturbance and the peak width, the said classification procedure shown in FIG. 16 enables rapid and simple judgement of classification patterns without detailed inspection of the entire data of the reference and pulse wave patterns. In particular, by performing the judgement of patterns D and E by detecting the number of peaks and degree of disturbance, it becomes possible to judge such anomalous data infallibly.

Unlike the usual anomalous data, it is difficult to make judgements in the classification of patterns A, B and C. However, these patterns can be classified accurately by using the data of the systolic pressure value Pmax. For example, even if peak width Pwidth is equal to or greater than n2, if systolic pressure value Pmax is small, it is a clinical error to deem the pattern to be pattern C and the pattern should be judged to be pattern B. Also, the classification of pattern A and pattern B should be performed on the basis of both systolic pressure Pmax and maximum value Pm (=PA(Peak)) of the pulse wave amplitudes. For example, if systolic pressure Pmax is no more than 100 and if maximum value Pm of the pulse wave amplitude is approximately ⅓ or less of the usual value (statistical mean) at the same time, the pattern may be classified as pattern B. However, if only one of the above conditions are met, a more appropriate classification result is that the pattern corresponds to both pattern A and pattern B.

The measured pulse wave pattern may thus be classified as corresponding to 2 or more of the said classification patterns by the classification procedure shown in FIG. 16. In this case, for example, if the subject moves his/her body during the measurement, the pulse wave pattern may become disrupted and be classified as corresponding to pattern C, D or E even if the subject is normal. However, since there are cases of multiple symptoms and intermediate cases, pulse wave patterns should be classified as corresponding to 2 or more reference patterns in such cases. Also, since the purpose of the said pattern classification is not to determine the final diagnosis result but is to call the necessary attention to the subject and the person diagnosing to promote a more accurate diagnosis than was possible formerly and to avoid pathological dangers, that a measured pattern is classified as corresponding to a plurality of reference patterns does not lower the value of the present invention by any means.

Figure 19:
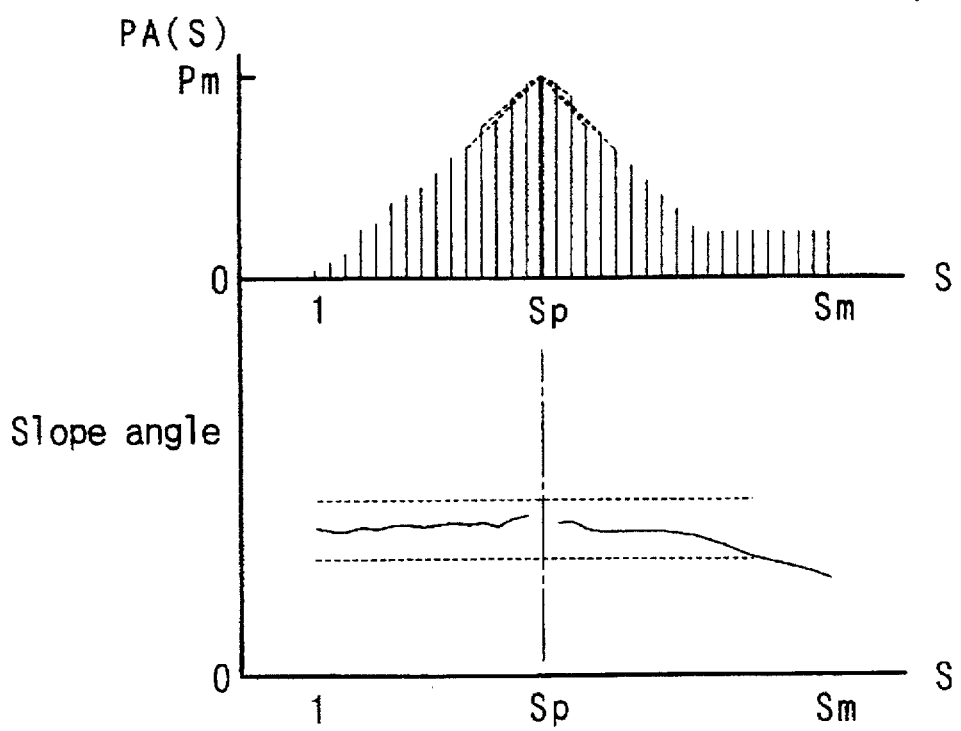
FIG. 19 is a graph which shows an example of a pulse wave pattern corresponding to pattern A for explaining the classification method of a different pattern classification means.
Figure 20:
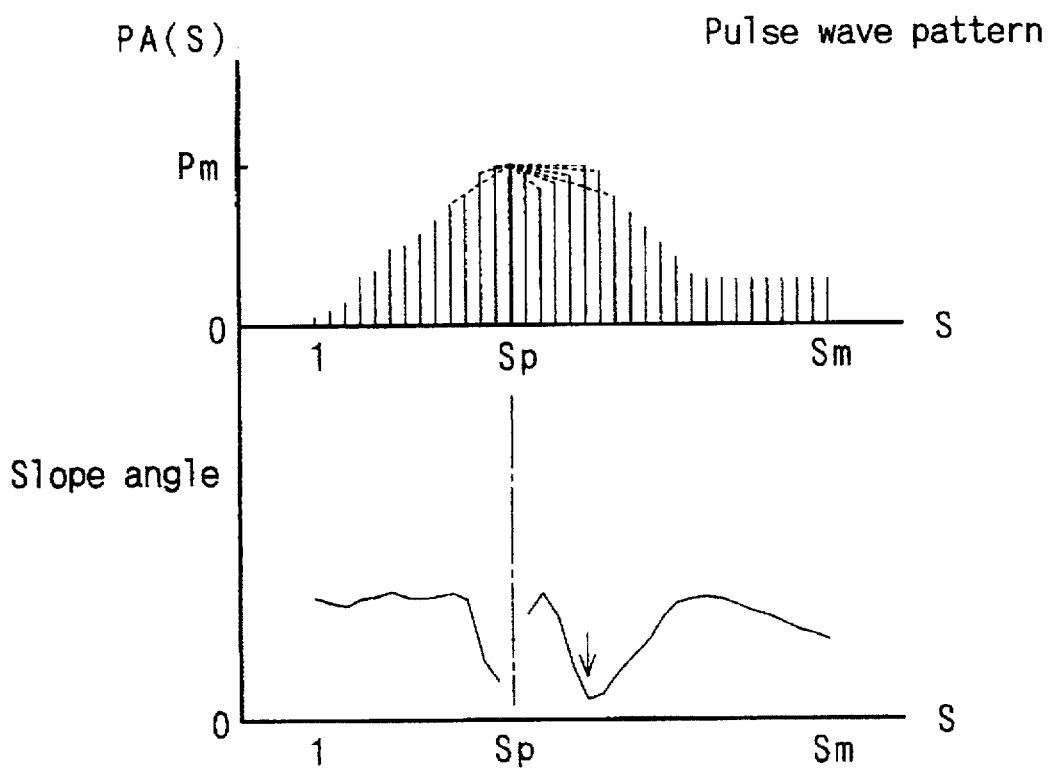
FIG. 20 is a graph which shows an example of a pulse wave pattern corresponding to pattern E for explaining the same classification method as that in FIG. 19.
Figure 21:
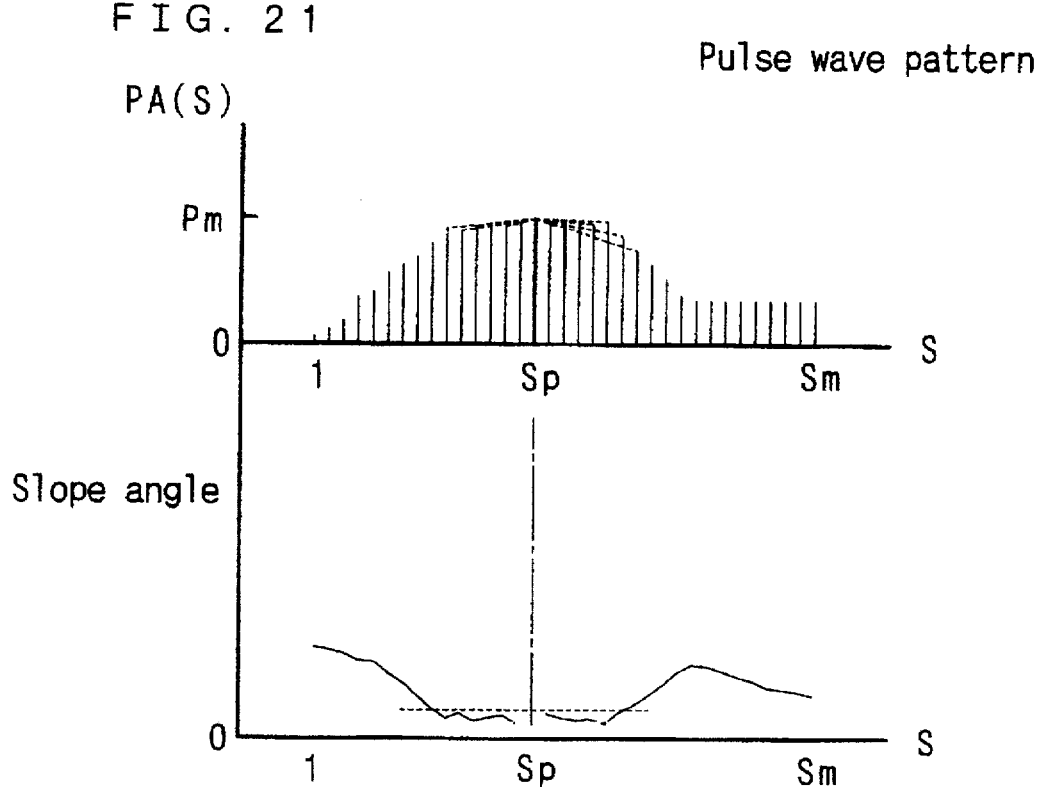
FIG. 21 is a graph which shows an example of a pulse wave pattern corresponding to pattern C for explaining the same classification method as that in FIG. 19.
Figure 22:
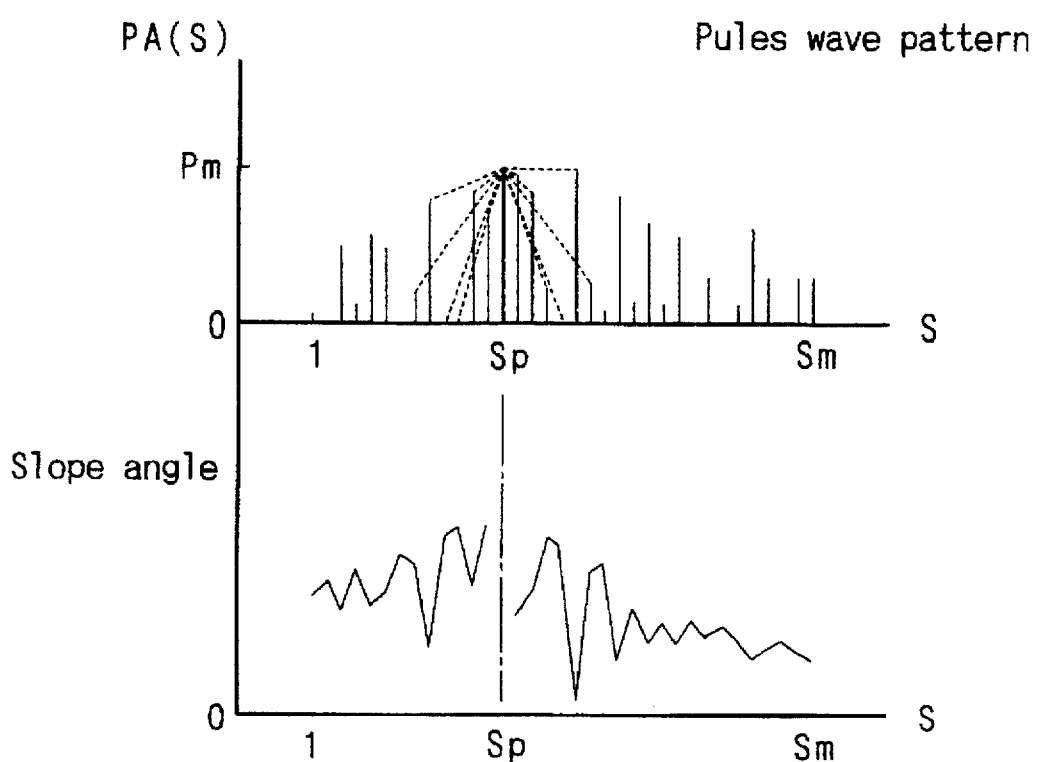
FIG. 22 is a graph which shows an example of a pulse wave pattern corresponding to pattern D for explaining the same classification method as that in FIG. 19.

Although 2 typical examples of pattern classification procedures were described in the embodiment above, the present invention is not limited by the said classification procedures and may be carried out by other classification procedures. An example is a method in which the slopes, of a straight line joining a point on the pattern that indicates the said maximum value Pm of PA(Sp) and a point on the pattern that indicates a value of PA(S) for which S≠Sp, are scanned sequentially from S=Sp in the forward and reverse directions as shown in FIGS. 19 to 22. In this method, the measured pattern is deemed to correspond to either pattern A or B if the values of the slopes are within a certain range as shown in FIG. 19. If, as shown in FIG. 20, the slope changes largely in the vicinity of S=Sp, the measured pattern corresponds to pattern E. If, as shown in FIG. 21, the slope is small in the vicinity of S=Sp and begins to increase some distance away from S=Sp, the measured pattern corresponds to pattern C. If, as shown in FIG. 22, the width of deflection of the slope is large or the slope deflects randomly, the measured pattern corresponds to pattern D. Thus, it is adequately possible to classify patterns according to the manner of variation of the slope angles by determining the slope angles of lines connecting points on the pattern in the manner above.

Although the pattern classification procedures in each of the embodiments described above were carried out by judging which of the 5 typical reference patterns the pulse wave pattern based on measured data resembled most closely, the reference patterns are not limited to those mentioned above and, if necessary, the physician may set his/her own unique reference patterns for each individual patient. Reference patterns that are different from those mentioned above may also be set by statistically processing the data measured for several patients. In such cases, 6 or more or less than 5 reference patterns may be set. From the data from preliminary tests performed by the present inventors, it was found that is possible to classify the measured data into approximately 10 or more patterns and to presume, in medical terms, the conditions of the circulatory system that can be associated with each of these patterns. On the other hand, there may be cases wherein measurements are made on the basis of a specific purpose. For example, if measurements are to be made only for the purpose of diagnosing arteriosclerosis, a relatively few number of reference patterns, for example, 2 or 3 patterns, may be prepared from the peak height, peak width, shape of the tip of the peak, etc. to carry out the classification.

Industrial Application

As described above, since the present invention is characterized by generating patterns of variations of pulse wave amplitudes and by classifying such patterns according to reference patterns or reference values or normalizing the pattern with a predetermined reference value, the present invention presents the following effects:

(1) Not only can pulse wave patterns be used to simply judge the blood pressure as was done conventionally, but the shapes of pulse wave patterns can be classified on the basis of hemodynamic references.

(2) The provision of a pulse wave pattern normalization means enables the recognition of only the shapes of pulse wave patterns which vary widely due to measurement conditions and individual differences. In particular, when a pulse wave pattern classification means is provided, it becomes possible to perform appropriate classification on the basis of only the pattern shapes.

(3) By setting a plurality of reference patterns, particularly according to peak shape, for the classification of pulse wave patterns, it becomes possible to obtain information on the expandability, etc. of blood vessels.

(4) By providing a means of quantizing the detected data, it becomes possible to priorly eliminate the amount of data that is unnecessary for subsequent pattern generation and classification and thus to reduce the processing time and the memory capacity.

(5) By detecting the peak and the degree of disturbance in the classification of pulse wave patterns, it becomes possible, particularly in the classification of anomalous patterns, to make the processing more rapid and simple.

(6) By detecting the peak width in the classification of pulse wave patterns, the classification process, that is pursuant to blood vessel conditions that are hard to distinguish, can be carried out infallibly.

(7) By using the simultaneously detected systolic pressure value as part of the classification references in the classification of pulse wave patterns, the classification process, that is pursuant to output strengths and blood vessel conditions that are difficult to distinguish, can be carried out accurately.

What is claimed is:

1. An electronic pressure detecting device for monitoring hemodynamic states of a patient based on dynamic characteristics of blood vessels or cardiac output characteristics comprising:

a cuff for applying cuff pressure to said patient;

pressure detection means for detecting said cuff pressure and pulse waves overlaid on said cuff pressure while said cuff pressure is gradually increased decreased;

pulse wave extraction means for extracting pulse wave components from said detected cuff pressure;

pulse wave amplitude detection means for detecting pulse wave amplitudes of said extracted pulse wave components;

pulse wave interval detection means for detecting pulse wave intervals which correspond to time intervals or pressure intervals between adjacent extracted pulse wave components;

pulse wave pattern generation means for generating pulse wave patterns based on said pulse wave amplitudes and said pulse wave intervals;

pattern classification means for classifying said pulse wave patterns into one or more categories based on comparison with a plurality of predetermined hemodynamic reference patterns that correspond to particular dynamic characteristics of blood vessels or cardiac output characteristic each category representing a different hemodynamic condition; and display means for displaying said generated pulse wave patterns and information about said one or more categories into which said pulse wave patterns are classified.

2. An electronic pressure detecting device for monitoring hemodynamic states of a patient based on dynamic characteristics of blood vessels or cardiac output characteristics comprising:

a cuff for applying cuff pressure to said patient;

pressure detection means for detecting said cuff pressure and pulse waves overlaid on said cuff pressure while said cuff pressure is gradually increased or decreased;

pulse wave extraction means for extracting pulse wave components from said detected cuff pressure;

pulse wave amplitude detection means for detecting pulse wave amplitudes of said extracted pulse wave components;

pulse wave pattern generation means for generating pulse wave patterns that graphically express variations in said detected pulse wave amplitudes while said cuff pressure is gradually decreased or increased;

pattern classification means for classifying said pulse wave patterns into one or more categories based on comparison with a plurality of predetermined hemodynamic reference patterns that correspond to particular dynamic characteristics of blood vessels or cardiac output characteristic each category representing a different hemodynamic condition; and display means for displaying said generated pulse wave patterns and information about said one or more categories into which said pulse wave patterns are classified.

3. An electronic pressure detecting device as set forth in claim 1 or in claim 2, wherein said pattern classification means is provided with means for detecting numbers of peaks or degrees of disturbance of said pulse wave patterns for use as part of said reference patterns during classification of said pulse wave patterns.

4. An electronic pressure detecting device as set forth in claim 1 or in claim 2, wherein said pattern classification means is provided with means for detecting peak widths of said pulse wave patterns for use as part of said reference patterns during classification of said pulse wave patterns.

5. An electronic pressure detecting device as set forth in claims 1 or in claim 2, further comprising blood pressure detection means for detecting at least systolic pressure based on said extracted pulse wave components or said generated pulse wave patterns, wherein said pattern classification means classifies said pulse wave patterns using said detected systolic pressure as part of said reference patterns.

* * * * *

UNITED STATES PATENT AND TRADEMARK OFFICE
CERTIFICATE OF CORRECTION

PATENT NO. : 5,680,867
DATED : October 28, 1997
INVENTOR(S) : Hideaki Shimazu, et. al.

It is certified that error appears in the above-identified patent and that said Letters Patent is hereby corrected as shown below:

Col. 16, line 49, insert -- or -- between "increased" and "decreased";

Col. 17, line 1, cancel "characteristic" and substitute -- characteristics, --;

Col. 18, line 2, cancel "characteristic" and substitute -- characteristics, --.

Signed and Sealed this

Tenth Day of March, 1998

Attest:

BRUCE LEHMAN

*Attesting Officer*    Commissioner of Patents and Trademarks